United States Patent
Ferguson

(10) Patent No.: US 12,178,423 B2
(45) Date of Patent: Dec. 31, 2024

(54) DYNAMIC TENSIONING DEVICES FOR ORTHOPEDIC COMPRESSION

(71) Applicant: OSSISCURA, LLC, Portland, OR (US)

(72) Inventor: Chad M. Ferguson, Knoxville, TN (US)

(73) Assignee: OSSISCURA, LLC, Portland, OR (US)

( * ) Notice: Subject to any disclaimer, the term of this patent is extended or adjusted under 35 U.S.C. 154(b) by 383 days.

(21) Appl. No.: 17/538,789

(22) Filed: Nov. 30, 2021

(65) Prior Publication Data

US 2022/0167961 A1    Jun. 2, 2022

Related U.S. Application Data

(60) Provisional application No. 63/119,349, filed on Nov. 30, 2020.

(51) Int. Cl.
*A61B 17/04* (2006.01)
*A61B 17/06* (2006.01)
(Continued)

(52) U.S. Cl.
CPC .......... *A61B 17/0401* (2013.01); *A61B 17/06* (2013.01); *A61B 17/8019* (2013.01); *A61B 2017/00867* (2013.01); *A61B 2017/0404* (2013.01); *A61B 2017/0425* (2013.01); *A61B 2017/044* (2013.01); *A61B 2017/0496* (2013.01)

(58) Field of Classification Search
CPC .. A61F 2/28; A61F 2002/2828; A61F 2/2846; A61F 2002/285; A61F 2002/2853; A61F 2/30; A61F 2/30749; A61F 2002/30751; A61F 2/38; A61F 2/3877; A61B 17/0401; A61B 17/842; A61B 2017/00867; A61B 17/82; A61B 2017/00862; A61B 2017/0496; A61B 17/0487; A61B 17/06; A61B 17/8023; A61B 17/808; A61B 2017/0404; A61B 2017/0409; A61B 2017/044; A61B 2017/0464; A61B 17/0466; A61B 17/0469; A61B 17/06066; A61B 17/06166
See application file for complete search history.

(56) References Cited

U.S. PATENT DOCUMENTS 5,810,851 A   9/1998  Yoon
6,641,593 B1  11/2003 Schaller et al.
(Continued)

FOREIGN PATENT DOCUMENTS

EP   2150288 B1   4/2011

OTHER PUBLICATIONS https://www.aptos.cz/en/product/light-lift-spring-method, Light Lift—Spring Method web page, accessed Sep. 2020, 1 pg.
(Continued)

*Primary Examiner* — Katherine M Shi
(74) *Attorney, Agent, or Firm* — Husch Blackwell, LLP; Bryan D. Stewart

(57) ABSTRACT

Constructs, devices, and methods for dynamically compressing tissue. An exemplary construct comprises a dynamic tensioning device configured to be implanted in a subject and defining a suture-coupling site. The dynamic tensioning device may be deformable superelastically from a resting state to a stretched state. A suture may be connected to the dynamic tensioning device at the suture-coupling site.

13 Claims, 17 Drawing Sheets

(51) Int. Cl.
*A61B 17/80* (2006.01)
*A61B 17/00* (2006.01)

(56) References Cited

U.S. PATENT DOCUMENTS

| | | | |
|---|---|---|---|
| 7,338,441 B2 | 3/2008 | Houser et al. | |
| 8,303,591 B1* | 11/2012 | Foerster | A61B 17/0401 |
| | | | 606/326 |
| 8,398,641 B2 | 3/2013 | Wallace et al. | |
| 8,414,599 B1* | 4/2013 | Foerster | A61B 17/0466 |
| | | | 606/139 |
| 10,524,912 B2 | 1/2020 | Wei | |
| 2004/0097975 A1 | 5/2004 | Rose | |
| 2006/0184231 A1 | 8/2006 | Rucker | |
| 2008/0249597 A1 | 10/2008 | Russell et al. | |
| 2009/0287215 A1* | 11/2009 | Fisher | A61B 17/82 |
| | | | 606/280 |
| 2010/0137679 A1 | 6/2010 | Lashinski et al. | |
| 2012/0083848 A1* | 4/2012 | Gonzalez-Hernandez | |
| | | | A61B 17/0401 |
| | | | 606/281 |
| 2013/0090694 A1 | 4/2013 | Norris et al. | |
| 2013/0123785 A1 | 5/2013 | Fonte | |
| 2013/0138151 A1 | 5/2013 | Maahs et al. | |
| 2014/0336701 A1 | 11/2014 | Mclorg | |
| 2018/0014828 A1 | 1/2018 | Fonte et al. | |
| 2019/0216456 A1 | 7/2019 | Schultz | |
| 2019/0254652 A1 | 8/2019 | Stone et al. | |

OTHER PUBLICATIONS

The Institute of Materials, Minerals and Mining, "Nitinol Bone Plate Exploring the Elements Behind the Extraordinary Alloy", 2009, 100 pgs.

Lamprakis, Andreas A. et al., "Biomechanical testing of a shape memory alloy suture in a meniscal suture model", Arthroscopy, vol. 25, No. 6, Jun. 2009, Abstract only, 1 pg.

Muller, Christian W. et al., "A Novel Shape Memory Plate Osteosynthesis for Noninvasive Modulation of Fixation Stiffness in a Rabbit Tibia Osteotomy Model", BioMed Research International, 2015, 9 pgs.

Nespoli, Adelaide et al., "A new design of a Nitinol ring-like wire for suturing in deep surgical field", Materials Science and Engineering: C, vol. 56, Nov. 2015, Abstract only, 3 pgs.

Thomas, Shane, Authorized Officer, ISA/US, Commissioner for Patents, "International Search Report" in connection with related International Application No. PCT/US2021/061274, dated Mar. 9, 2022, 2 pgs.

Thomas, Shane, Authorized Officer, ISA/US, Commissioner for Patents, "Written Opinion of the International Searching Authority" in connection with related International Application No. PCT/US2021/061274, dated Mar. 9, 2022, 9 pgs.

Xu, W. et al., "Shape Memory Alloy Fixator System for Suturing Tissue in Minimal Access Surgery", Springer Link, Sep. 1999, Abstract only, 8 pgs.

* cited by examiner

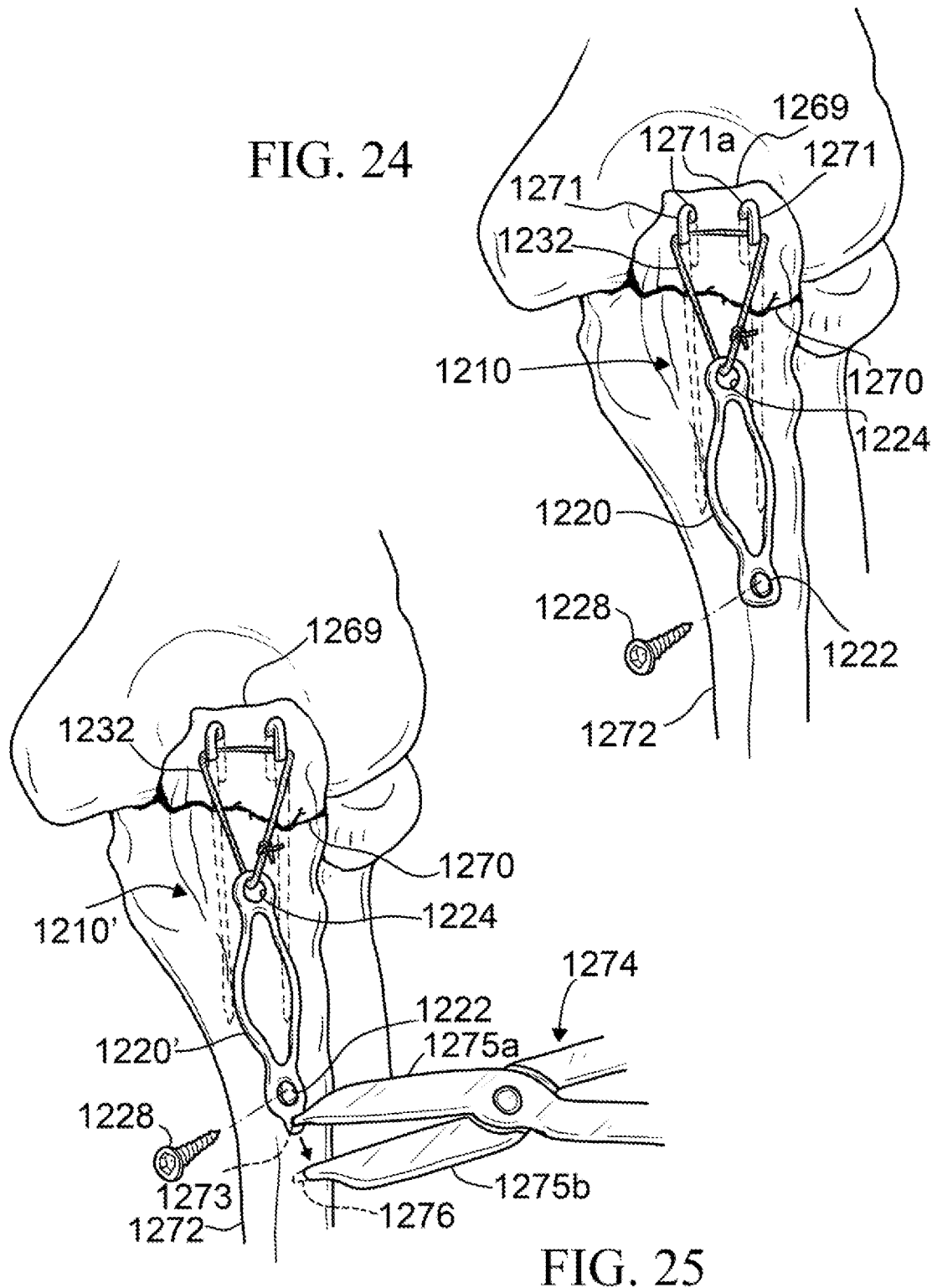

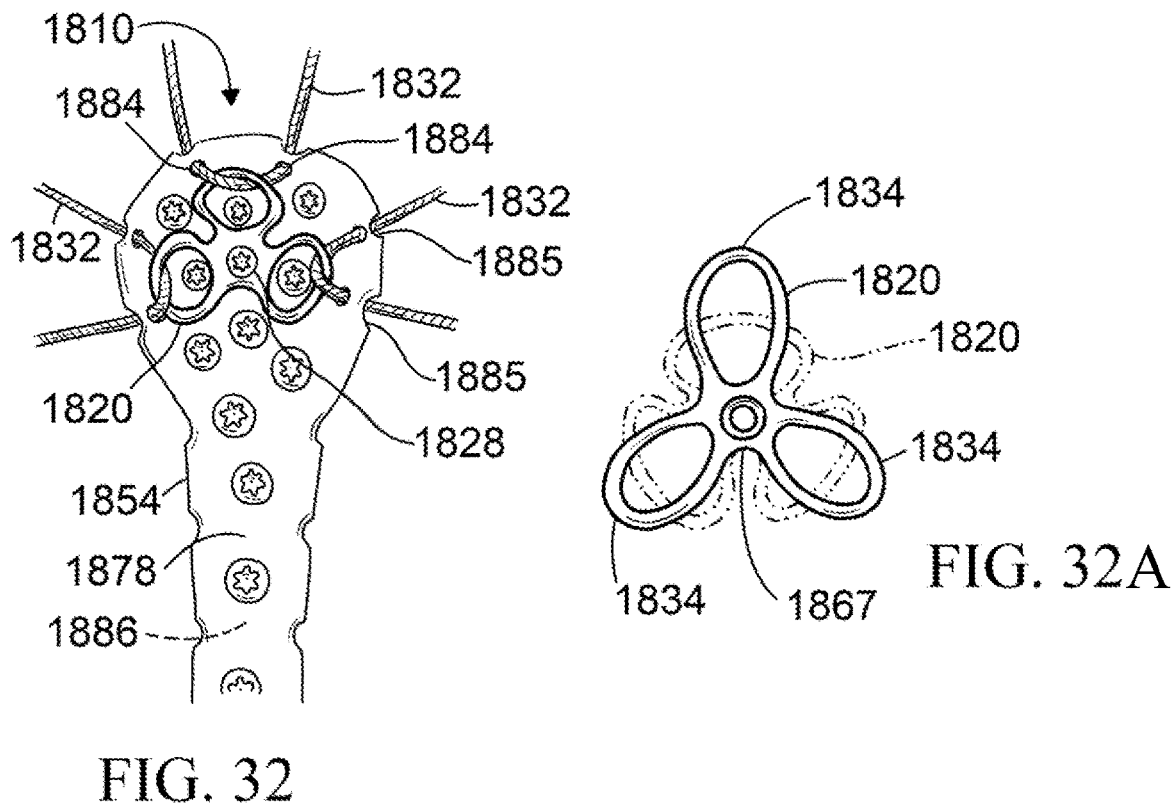
FIG. 32
FIG. 32A
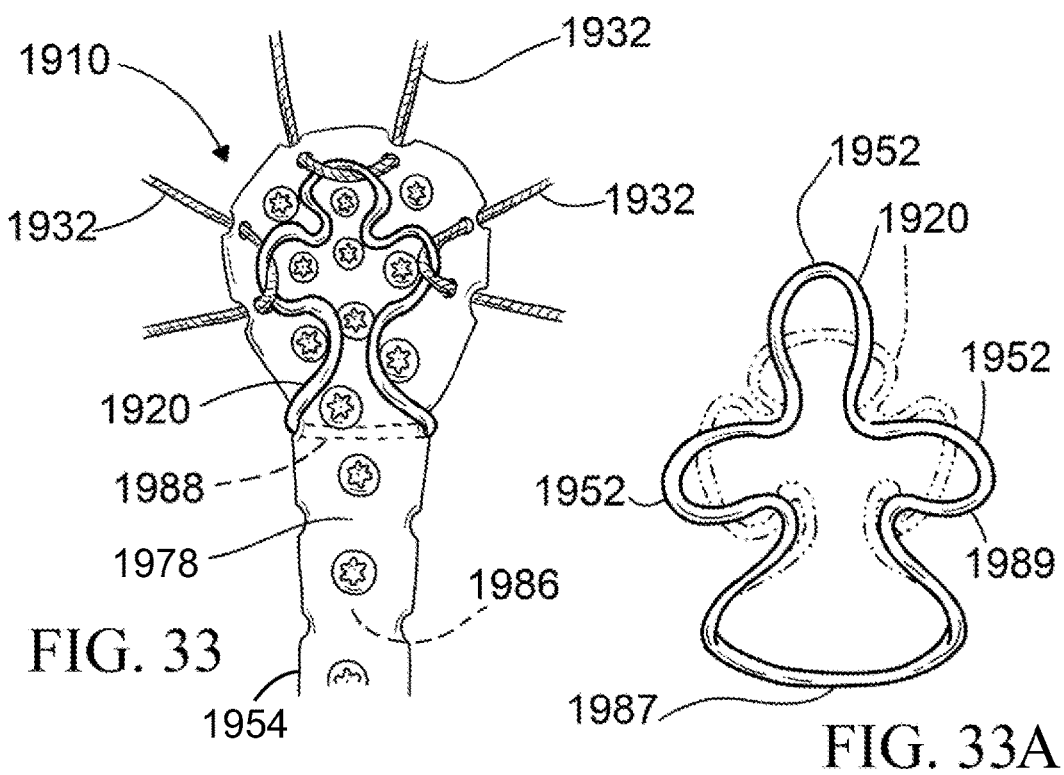
FIG. 33
FIG. 33A

DYNAMIC TENSIONING DEVICES FOR ORTHOPEDIC COMPRESSION

CROSS-REFERENCE TO PRIORITY APPLICATION

This application is based upon and claims the benefit under 35 U.S.C. § 119(e) of U.S. Provisional Patent Application Ser. No. 63/119,349, filed Nov. 30, 2020, which is incorporated herein by reference in its entirety for all purposes.

INTRODUCTION

Suture is often used in a subject to repair tissue that has been broken, torn, cut, replaced, or the like. The suture, alone or in combination with one or more associated devices, may be implanted by a surgeon to stabilize the position of tissue portions relative to one another while the tissue heals. To apply stable compression to tissue, the suture must be properly tensioned by the surgeon when implanted, and this tension maintained during the healing process. However, securing the suture under tension to tissue can be challenging in some surgical procedures. Moreover, even if suitably tensioned when implanted, the suture may lose its tension over time due to slippage, migration, and/or structural changes in the tissue, among others. A new approach is needed for establishing and maintaining tension on a surgically implanted suture.

SUMMARY

The present disclosure provides constructs, devices, and methods for dynamically compressing tissue. An exemplary construct comprises a dynamic tensioning device configured to be implanted in a subject and defining a suture-coupling site. The dynamic tensioning device may be deformable superelastically from a resting state to a stretched state. A suture may be connected to the dynamic tensioning device at the suture-coupling site.

BRIEF DESCRIPTION OF THE DRAWINGS

FIG. 24 is a partially exploded view of an exemplary compression construct fixing a fractured olecranon and including a dynamic tensioning device connected to a tension band.

FIG. 25 is a view of another exemplary compression construct being installed to fix a fractured olecranon and showing a tool to intraoperatively stretch a dynamic tensioning device of the compression construct.

FIG. 32 is a plan view of a compression construct including a bone plate and a dynamic tensioning device mounted on an outer surface of the bone plate and located within the two-dimensional footprint of the bone plate.

FIG. 32A is a plan view of the dynamic tensioning device of FIG. 32 taken in isolation, with a stretched state depicted in solid lines and a resting state in broken lines.

FIG. 33 is a plan view of another compression construct including a bone plate and a dynamic tensioning device coupled to the bone plate and located at least predominantly within the two-dimensional footprint of the bone plate.

FIG. 33A is a plan view of the dynamic tensioning device of FIG. 33 taken in isolation, with a stretched state depicted in solid lines and a resting state in broken lines.

DETAILED DESCRIPTION

Figure 1:
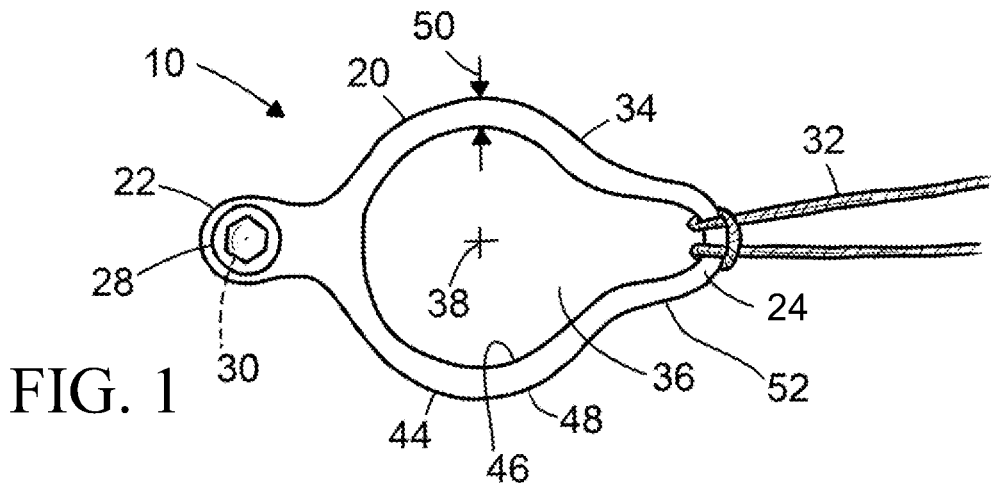
FIG. 1 is a fragmentary plan view of an exemplary compression construct including a dynamic tensioning device having a fixed coupling site anchored to underlying bone and a movable suture-coupling site connected to a suture, taken with the dynamic tensioning device in a resting state and in the absence of the underlying bone.

The present disclosure provides constructs, devices, and methods for dynamically compressing tissue. An exemplary construct comprises a dynamic tensioning device configured to be implanted in a subject and defining a suture-coupling site. The dynamic tensioning device may be deformable superelastically from a resting state to a stretched state. A suture may be connected to the dynamic tensioning device at the suture-coupling site.

The compression constructs, tensioning devices, and associated methods of the present disclosure may enable tensioning of sutures that is controllably established and robustly maintained. As a result, compression can be applied to tissues or tissue portions more reliably and consistently for improved surgical outcomes.

Further aspects of the present disclosure are described in the following sections: (I) definitions, (II) overview, (III) examples, components, and alternatives, (IV) illustrative combinations and additional examples, (V) advantages and benefits, and (VI) conclusion.

Features, functions, and advantages may be achieved independently in various examples of the present disclosure, or may be combined in yet other examples, further details of which can be seen with reference to the following description and drawings.

I. Definitions

Technical terms used in this disclosure have meanings that are commonly recognized by those skilled in the art. However, the following terms may be further defined as follows.

"Comprising," "including," and "having" (and conjugations thereof) are used interchangeably to mean including but not necessarily limited to, and are open-ended terms not intended to exclude additional, unrecited elements or method steps.

"Coupled" means to be in such relation that the performance of one influences the performance of the other, may include being connected, either permanently or releasably, whether directly or indirectly through intervening components.

"Exemplary" means "illustrative" or "serving as an example." Similarly, the term "exemplify" (or "exemplified") means "to illustrate by giving an example." Neither term implies desirability or superiority.

"First," "second," and similar terms are used to distinguish or identify various members of a group, or the like, in the order they are introduced in a particular context and are not intended to show serial or numerical limitation.

"Substantially" means to be predominantly conforming to the particular dimension, range, shape, concept, or other aspect modified by the term, such that a feature or component need not conform exactly, so long as it is suitable for its intended purpose or function. For example, a "substantially cylindrical" object means that the object resembles a cylinder, but may have one or more deviations from a true cylinder.

A "superelastic" material or device exhibits "superelasticity," also called pseudoelasticity. Superelasticity is an elastic response to an applied stress, caused by a phase transformation, such as within a shape-memory material. For example, the phase transformation may be between austenitic and martensitic phases of a crystal, as exhibited in shape-memory alloys. The superelasticity may be produced by reversible motion of domain boundaries during the phase transformation, rather than just bond stretching and/or the introduction of defects in a crystal lattice. Thus, a superelastic device or material may return to its previous (undeformed) shape after the removal of even relatively high applied strains (e.g., a strain of at least about 1%, 2%, or 5%, among others). Superelastic materials belong to the larger family of shape-memory materials. When mechanically loaded, a superelastic material may deform superelastically to very high strains by the creation of a stress-induced phase. When the load is removed, the stress-induced phase may become unstable, such that the material regains its original shape.

Any of the devices or constructs (or portions thereof) of the present disclosure may be superelastic and/or formed at least partially or predominantly (greater than 50% by weight/volume) of a superelastic material. The superelastic material may be metal or a polymer, among others. Exemplary superelastic metals that may be suitable include metal alloys, such as alloys including nickel and titanium (i.e., nickel-titanium alloys). The nickel-titanium alloy may have any suitable percentage of nickel and titanium collectively, such as 10-100% or 50-100%, and any suitable percentage nickel or titanium, such as 10-90%, 20-80%, 30-70%, or 40-60%, among others.

The term "suture," as used herein, means any long, slender, flexible member for surgical use, typically being biocompatible such that the suture is implantable in a subject. Suture may have a substantially uniform diameter or the diameter may vary along the longitudinal axis of the suture. The suture may be round, oval, or flattened in cross-section, among others. A suture, also called a length of suture, may be composed of only a single strand or two or more discrete strands, which may be connected to one another (such as entwined or attached end-to-end). Suitable materials for suture include metal, synthetic/natural polymer (s), and/or the like. Exemplary suture includes cord, wire, tape, cable, and/or the like.

The term "unitary" means having no removable parts, and/or structured or functioning as a single piece. In some cases, a device or component that is unitary may have portions that are "formed integrally" with one another, which means that the portions collectively are formed as a single piece.

II. Overview

This section provides an overview of the compression constructs, dynamic tensioning devices, and associated methods of the present disclosure.

An exemplary construct to compress tissue is provided. The construct comprises a dynamic tensioning device configured to be implanted in a subject and defining a suture-coupling site. The dynamic tensioning device is deformable superelastically from a resting state to a stretched state. A suture is connected to the dynamic tensioning device at the suture-coupling site. In some examples, the tensioning device includes at least two predefined suture-coupling sites, each of which may be connected to a suture. In some examples, the tensioning device includes three or more predefined suture-coupling sites. In some examples, the tensioning device also includes an anchoring site, and the construct comprises a device anchor (e.g., a threaded fastener) configured to anchor the anchoring site to bone. In some examples, the tensioning device includes a plurality (e.g., 2, 3, or more) superelastic loops (and/or superelastic arms), each defining a suture-coupling site. The superelastic loops and/or arms are more flexible and deformable than a body of the tensioning device. In some examples, the tensioning device includes a structural member forming a closed loop, and the closed loop includes a plurality of radial protrusions. In some examples, the tensioning device is configured to be hooked radially onto one or more suture regions. In some examples, the tensioning device is configured to extend along a tunnel formed in bone.

A method of tissue compression is provided. In the method, a dynamic tensioning device is selected. The tensioning device is deformable superelastically from a resting state to a stretched state. A first tissue or tissue portion and a second tissue or tissue portion are connected to one another using the dynamic tensioning device coupled to one or more sutures and disposed in the stretched state.

III. Examples, Components, and Alternatives

The following subsections, A-K, relate to compression constructs, dynamic tensioning devices, and associated methods of the present disclosure. The examples described in these subsections are intended for illustration and should not be interpreted as limiting the entire scope of the present disclosure. Each subsection may include one or more distinct examples, and/or contextual or related information, function, and/or structure.

A. Overview of Compression Constructs

This subsection provides an overview of illustrative compression constructs each including a dynamic tensioning device, and methods of using the compression constructs to compress tissue; see FIGS. 1-13. Each dynamic tensioning device of the present disclosure may be unitary and is composed at least partially or predominantly of a superelastic material, such as a nickel-titanium alloy, and thus is superelastically deformable.

Figure 2:
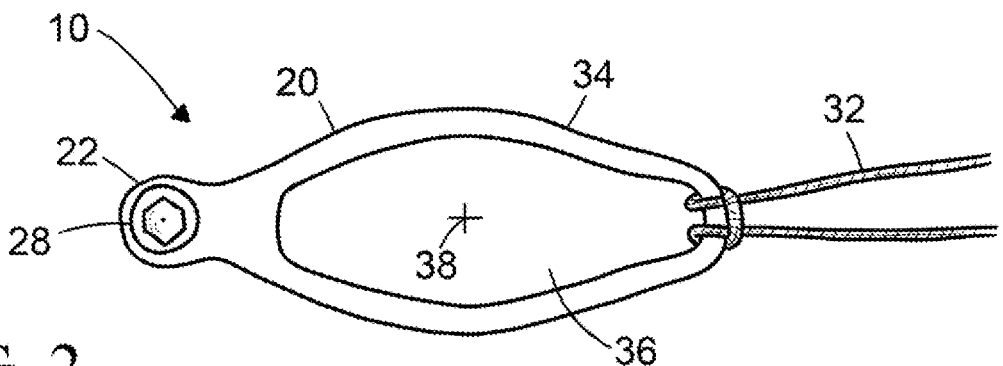
FIG. 2 is another fragmentary plan view of the compression construct of FIG. 1, taken as in FIG. 1 except with the dynamic tensioning device in a stretched state produced by superelastic deformation.
Figure 3:
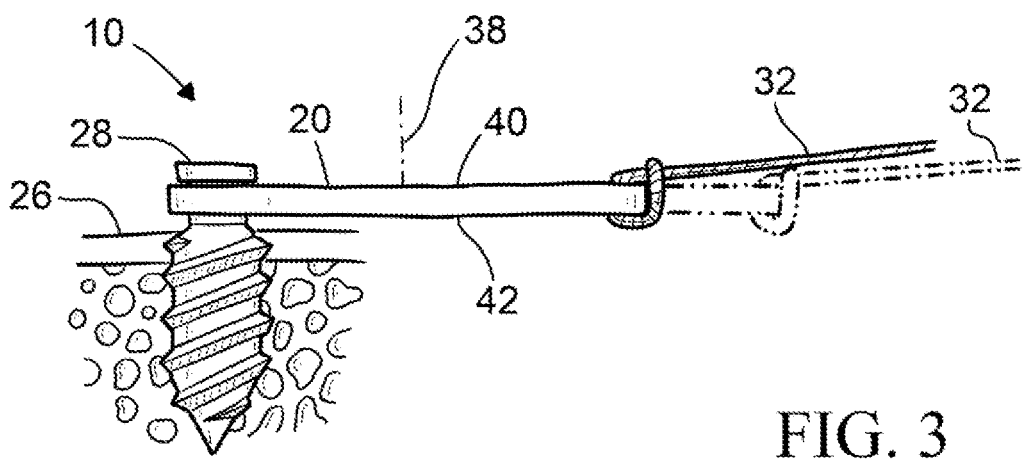
FIG. 3 is an edge view of the compression construct of FIGS. 1 and 2, taken in the presence of underlying bone, with the positions of the compression construct corresponding to FIGS. 1 and 2 shown in solid lines and broken lines, respectively.

FIGS. 1-3 show an exemplary compression construct 10 including a dynamic tensioning device 20. Tensioning device 20 is superelastically deformable from a resting (or contracted) state (see FIG. 1) to a stretched (or expanded) state (see FIG. 2). The tensioning device may be transitioned between the resting state and various stretched states by changing the mechanical load/stress on the tensioning device.

Tensioning device 20 defines a pair of coupling sites, namely, an anchoring site 22 and a suture-coupling site 24, at which the tensioning device is connected to other components of compression construct 10. The anchoring and suture-coupling sites are spaced from one another, such as positioned at opposite end regions or opposite side regions of tensioning device 20.

Anchoring site 22 is anchored to underlying bone 26 using a device anchor 28. The device anchor may be a linear fastener that extends through an aperture 30 defined by tensioning device 20 and into underlying bone 26. In the depicted example, device anchor 28 is an externally-threaded fastener, but other types of fasteners or assemblies may be suitable. The device anchor prevents translational movement of a local portion (e.g., one end) of tensioning device 20, with respect to underlying bone, and may prevent or permit rotation of the tensioning device about an axis defined by the device anchor.

Suture-coupling site 24 is connected to, and optionally engaged with, a suture 32 (interchangeably called a length of suture). The suture is also connected to tissue independently of tensioning device 20. For example, one end region of suture 32 may be connected to suture-coupling site 24 and an opposite end region of suture 32 may be connected to the tissue directly or through one or more additional components of compression construct 10 (e.g., using a suture anchor).

Tensioning device 20 forms a closed loop 34 defining a central opening 36. A central axis 38 extends through central opening 36, and is oriented transverse to an outer surface 40 and an inner surface 42 of tensioning device 20. Inner surface 42 is opposite outer surface 40 and faces underlying bone 26. Tensioning device 20 includes a structural member 44 (e.g., a strip) that extends completely around central axis 38 and circumferentially bounds central opening 36. Structural member 44 has an inner edge 46 and an outer edge 48, and a width 50 measured between the inner edge and the outer edge. The width (e.g., an average of width 50 along the structural member) may be less than a length and/or a width of closed loop 34, such as less than 50% or 25% of the length and/or the width. Width 50 may be generally uniform along structural member 44, or may increase locally to create a region(s) of structural member 44 at which deformation is discouraged and/or to enable formation of an aperture(s) (e.g., aperture 30), and/or may decrease locally to create a region(s) of structural member 44 at which deformation is encouraged.

Structural member 44 may be located at a varying distance from central axis 38 in the resting state of tensioning device 20 (see FIG. 1). The distance may increase locally along structural member 44 to form a radial protrusion 52 corresponding to suture-coupling site 24. Suture 32 extends through central opening 36 at radial protrusion 52 and is held at this position naturally as compression construct 10 is tensioned, to minimize tension on suture 32. In other examples, central opening 36 is absent. In other examples, suture-coupling site 24 is separate from central opening 36 (see below).

FIG. 2 shows tensioning device 20 in a stretched state produced by superelastic deformation. In the stretched state, the distance between anchoring site 22 and suture-coupling site 24 is increased relative to the resting state of FIG. 1. When opposite ends of compression construct 10 are connected to spaced tissues or tissue portions, tensioning device 20 in the stretched state can increase the tension on suture 32 because anchoring site 22 and suture-coupling site 24 are urged toward one another by potential energy stored in the tensioning device through superelastic deformation.

FIG. 3 shows tensioning device 20 shaped as a plate. However, the tensioning device is not necessarily planar. In other words, the tensioning device may have contoured, nonplanar outer and inner surfaces 40, 42 to match a surface contour of a bone on which the tensioning device is installed.

Figure 4:
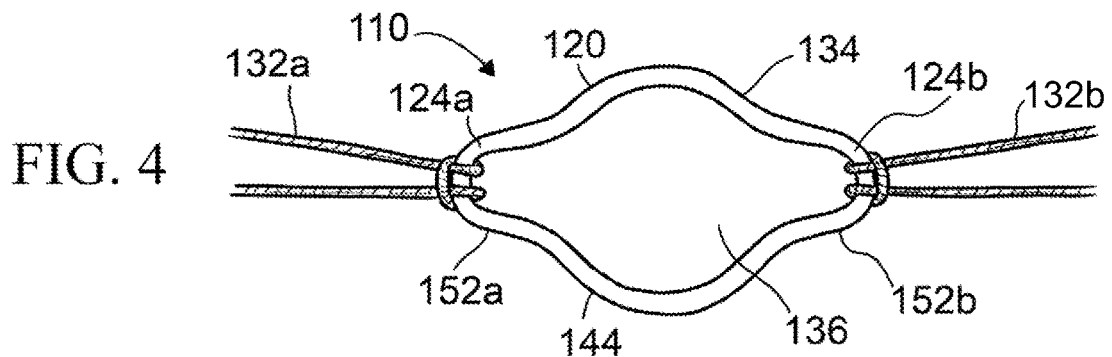
FIG. 4 is a fragmentary plan view of an exemplary compression construct including a dynamic tensioning device having a pair of movable suture-coupling sites each connected to a suture, taken with the dynamic tensioning device in a resting state and in the absence of underlying bone.
Figure 5:
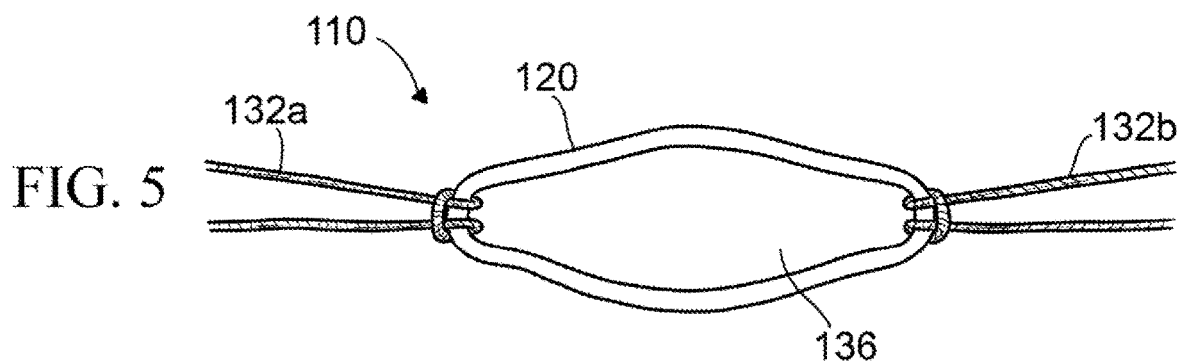
FIG. 5 is another fragmentary plan view of the compression construct of FIG. 1, taken as in FIG. 4 except with the dynamic tensioning device in a stretched state produced by superelastic deformation.

FIGS. 4 and 5 show another exemplary compression construct 110 including a dynamic tensioning device 120. The tensioning device is shown in a resting state (FIG. 4) and a stretched state (FIG. 5). Tensioning device 120 has a pair of predefined suture-coupling sites 124a, 124b each connected to a respective suture 132a, 132b. Neither suture-coupling site 124a, 124b is anchored to underlying bone and thus both of the suture-coupling sites can move along the underlying bone if the tension on compression construct 110 changes.

Tensioning device 120 has a structural member 144 extending completely around a central axis 138 to form a closed loop 134. Structural member 144 forms a pair of radial protrusions 152a, 152b located opposite one another and each corresponding to one of suture-coupling sites 124a, 124b. Accordingly, sutures 132a, 132b each extend through a central opening 136 of tensioning device 120.

When opposite ends of compression construct 110 are connected to tissue, tensioning device 120 in the stretched state can increase the tension on both sutures 132a, 132b, because suture-coupling sites 124a, 124b are urged toward one another by potential energy stored in the tensioning device through superelastic deformation.

Figures 6, 7:
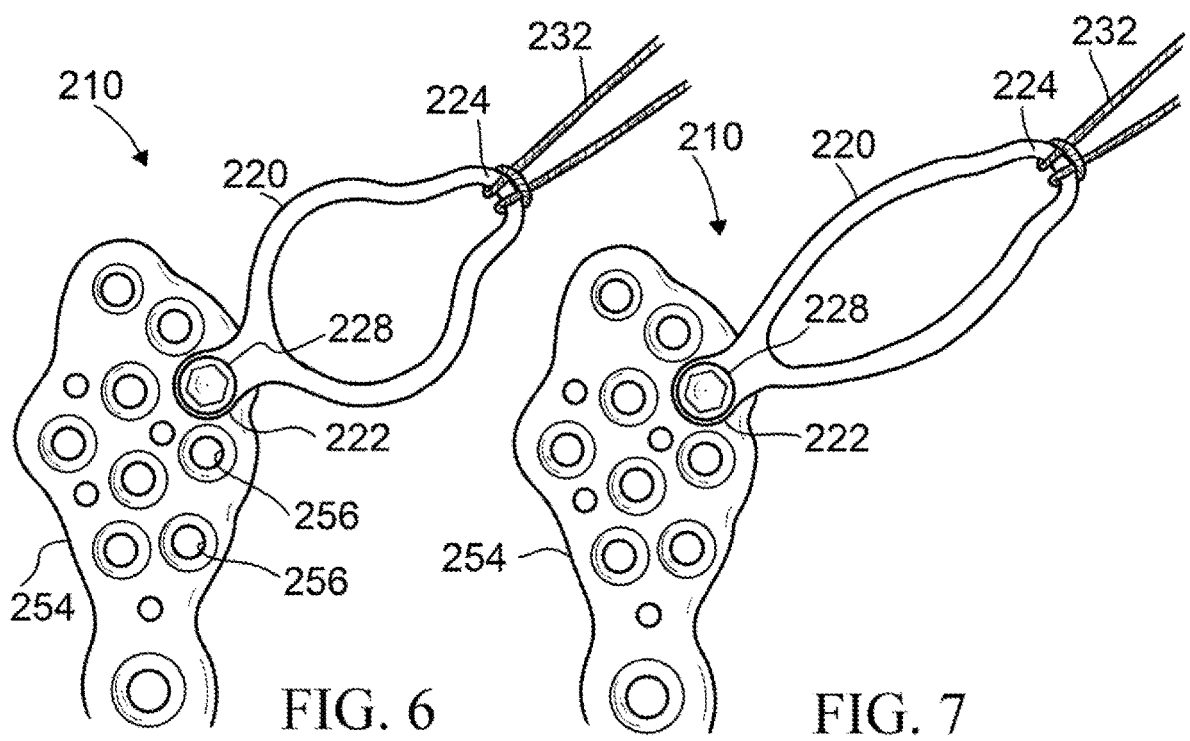
FIG. 6 is a fragmentary plan view of an exemplary compression construct including a dynamic tensioning device having a fixed coupling site anchored to underlying bone via a bone plate, and a movable suture-coupling site connected to a suture, taken with the dynamic tensioning device in a resting state and in the absence of the underlying bone.
FIG. 7 is another fragmentary plan view of the compression construct of FIG. 6, taken as in FIG. 6 except with the dynamic tensioning device in a stretched state produced by superelastic deformation.

FIGS. 6 and 7 show yet another exemplary compression construct 210 including a dynamic tensioning device 220 and a suture 232. The tensioning device is shown in a resting state (FIG. 6) and a stretched state (FIG. 7). Tensioning device 220 has an anchoring site 222 and a suture-coupling site 224.

Compression construct 210 is similar to compression construct 10 (also see FIGS. 1-3), except that compression construct 210 includes a bone plate 254 on which anchoring site 222 is mounted using a device anchor 228. Bone plate 254 defines a plurality of apertures 256 for receiving fasteners, such as bone screws, that mount the bone plate to underlying bone. Device anchor 228 extends into one of apertures 256 and optionally into underlying bone. In some cases, device anchor 228 is disposed in threaded engagement with an internal thread of an aperture 256 of bone plate 254. In some cases, device anchor 228 is disposed in threaded engagement with underlying bone. The device anchor prevents translational movement of one end of tensioning device 220, and may prevent or permit or rotation of the tensioning device about an axis defined by the device anchor.

Figure 8:
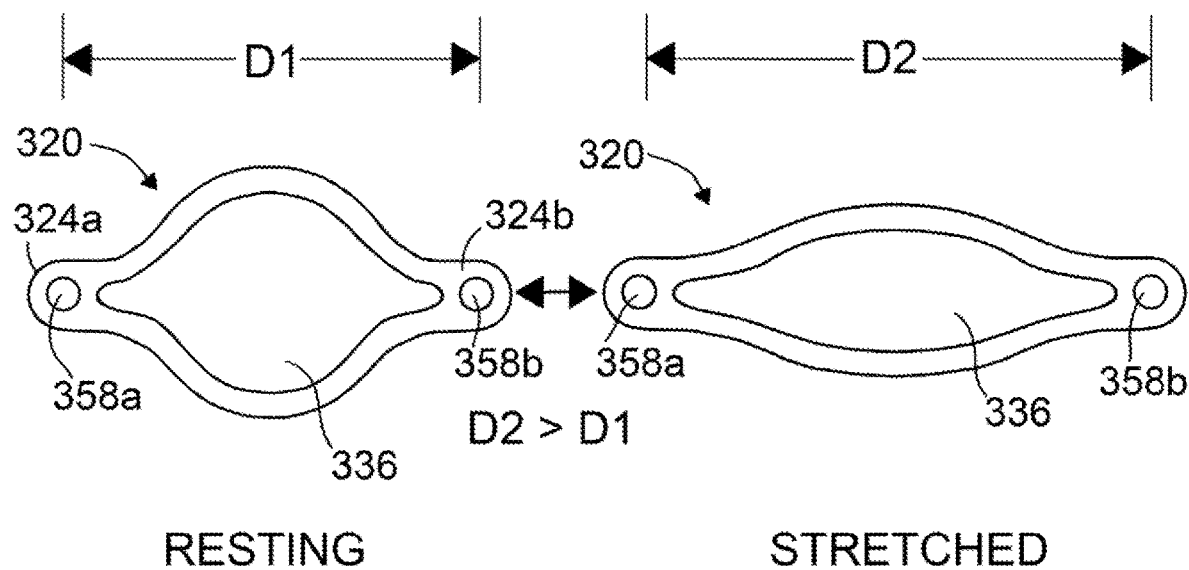
FIG. 8 is a deformation diagram for another exemplary dynamic tensioning device, taken with the tensioning device converted between a resting state and a stretched state.

FIG. 8 shows another exemplary dynamic tensioning device 320. Tensioning device 320 is similar to tensioning device 120 (also see FIGS. 4 and 5), except that that each suture-coupling site 324a, 324b is defined by a respective aperture 358a, 358b. The apertures are separate from a central opening 336. The distance (D) between apertures 358a, 358b is smaller in the resting state (D1) than the stretched state (D2).

Figure 9:
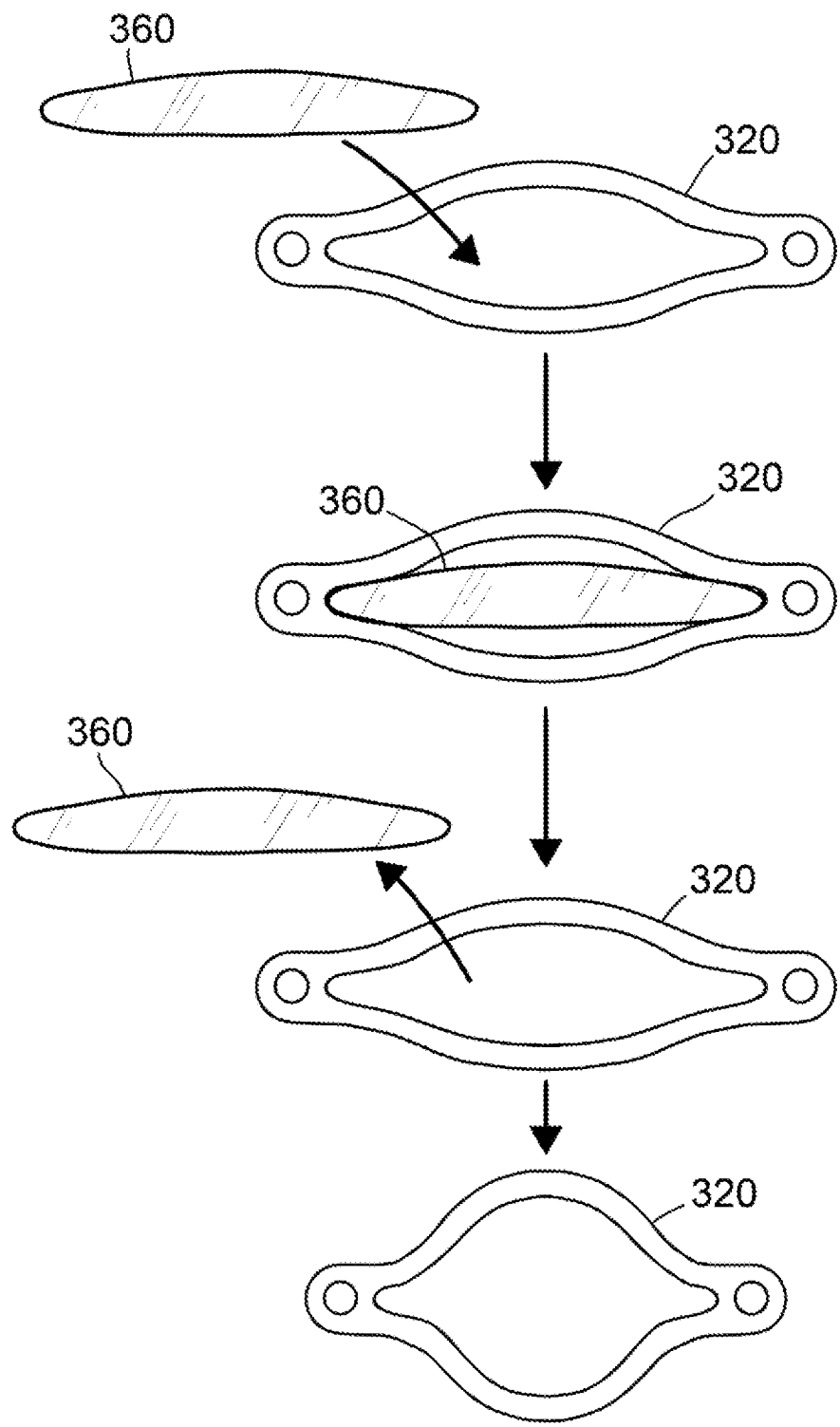
FIG. 9 is a schematic flow diagram illustrating use of a retainer to hold the dynamic tensioning device in the stretched state of FIG. 8.

FIG. 9 illustrates use of an exemplary retainer 360 to hold tensioning device 320 in a stretched state. The retainer may be assembled with the tensioning device, such as when the tensioning device is being stretched by applied tension or when the tensioning device is deformed below the transition temperature of the material forming the device. Once the retainer is removed and/or disabled, the tensioning device can return to, or at least towards, the resting state. The retainer may be removed and/or disabled once a compression construct incorporating the tensioning device has been assembled and connected to tissues and/or tissue portions.

Figure 10:
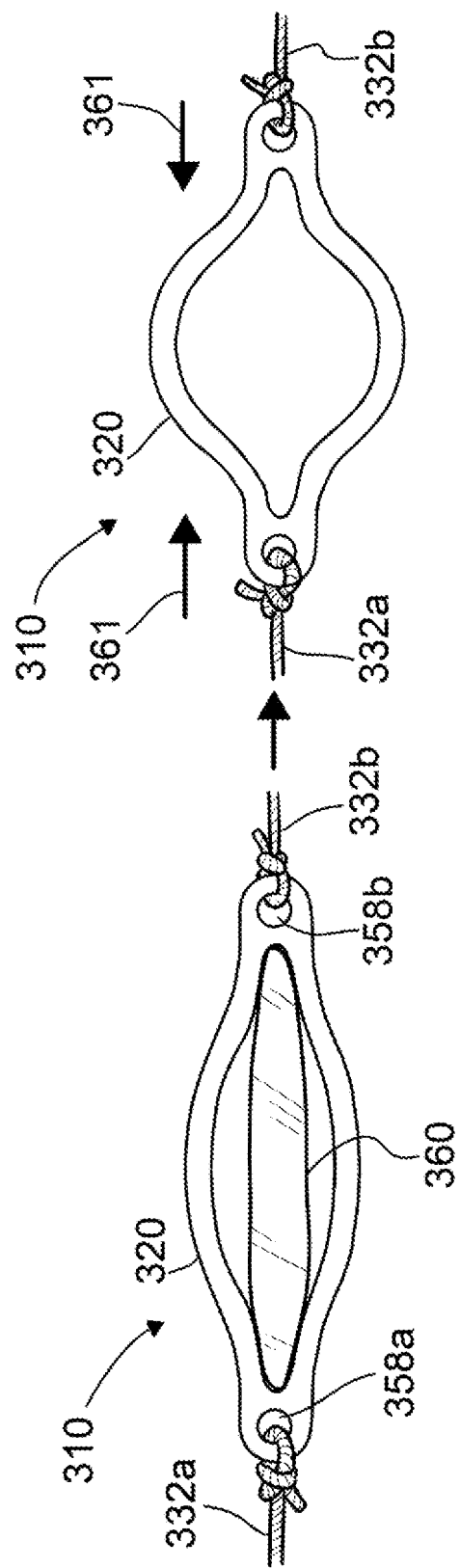
FIG. 10 is a schematic flow diagram illustrating application of tension to sutures using the dynamic tensioning device and retainer of FIGS. 8 and 9.

FIG. 10 illustrates how a compression construct 310 including tensioning device 320 can apply compression to tissue via additional implanted components, such as a pair of sutures 332a, 332b. The tensioning device may be connected to sutures 332a, 332b, while the tensioning device remains held in the stretched state by retainer 360. The other end of each suture 332a, 332b may be attached to a respective tissue or tissue portion. Retainer 360 then may be removed/disabled, which allows the tensioning device to return toward the resting state, which results in compression 361 on the tissues or tissue portions.

Figure 11:
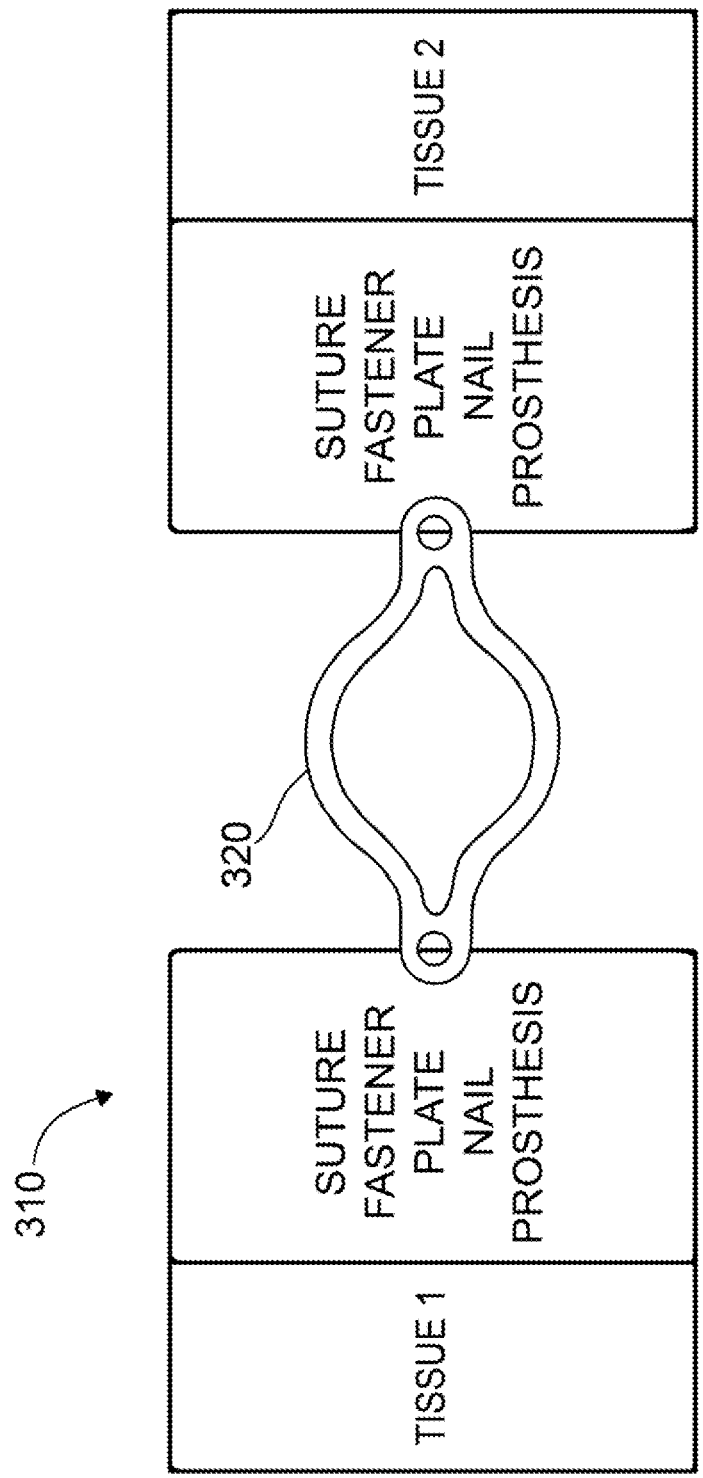
FIG. 11 is a schematic diagram listing exemplary components of a compression construct connected to a pair of tissues or tissue portions.

FIG. 11 schematically illustrates different combinations of components for a compression construct 310 including tensioning device 320 (or any other tensioning device of the present disclosure). The construct is shown secured to and connecting a first tissue or tissue portion ("Tissue 1") to a second tissue or tissue portion ("Tissue 2"). Each tissue or tissue portion may be hard (i.e., bone) or soft (e.g., ligament, tendon, or muscle). Each tissue or tissue portion may be connected to the tensioning device at one of apertures 358a, 358b (and/or a coupling site, such as an anchoring site or a suture-coupling site) by any suitable implantable component(s) for spanning the distance between the tissue or tissue portion and the aperture or site. Exemplary implantable components include one or more sutures, a fastener (e.g., a screw), a bone fixation device (e.g., a bone plate, pin, intramedullary nail, etc.), a prosthesis, or a combination thereof, among others.

Figure 12:
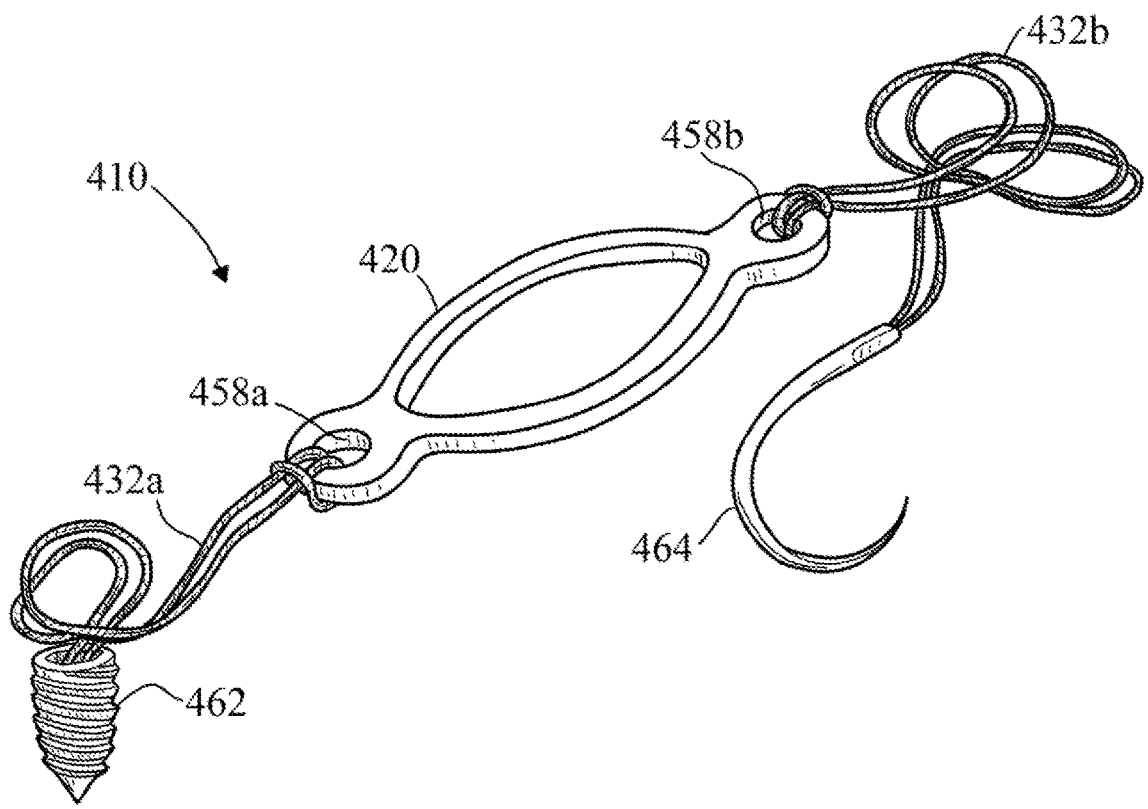
FIG. 12 is a view of an exemplary compression construct including a dynamic tensioning device, a pair of separate sutures, a needle, and a suture anchor.

FIG. 12 shows an example of a compression construct 410 for connecting bone (hard tissue) to soft tissue and applying compression between these tissues. The compression construct includes a dynamic tensioning device 420 defining a pair of apertures 458a, 458b. Two separate sutures 432a, 432b are connected to the tensioning device at apertures 458a, 458b. Suture 432a is connected at one end to a suture anchor 462, which is configured to be placed into bone. The other suture 432b is attached at one end to a needle 464 for threading the suture through soft tissue, such as tendon, ligament, or muscle.

Figure 13:
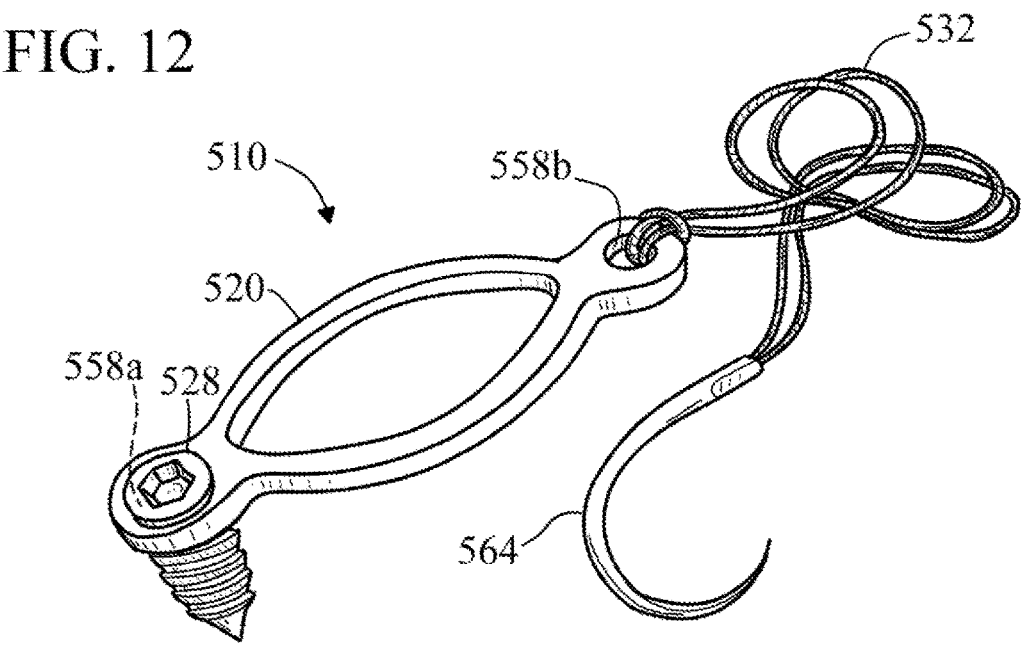
FIG. 13 is a view of an exemplary compression construct including a dynamic tensioning device, a pair of separate sutures, a needle, and an anchor for a fixed coupling site of the tensioning device.

FIG. 13 shows another example of a compression construct 510 for connecting hard tissue to soft tissue and applying compression between these tissues. The construct includes a dynamic tensioning device 520 defining a pair of apertures 558a, 558b. One aperture 558b of the tensioning device is attached to a suture 532, which in turn is connected to a needle 564, and the other aperture 558a of the tensioning device is assembled with device anchor 528 for securing a portion of tensioning device 520 around aperture 558a to bone (also see compression construct 10 of FIGS. 1-3).

B. Multi-Lobed Dynamic Tensioning Devices

This subsection describes illustrative dynamic tensioning devices having multiple lobes, and exemplary use of the dynamic tensioning devices in a compression construct with suture to fix a fractured patella; see FIGS. 14-19.

Figure 14:
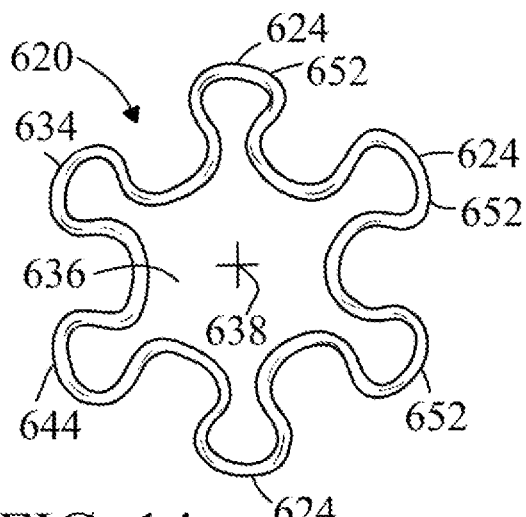
FIG. 14 is a plan view of an exemplary multi-lobed dynamic tensioning device, taken with the tensioning device in a resting state.
Figure 15:
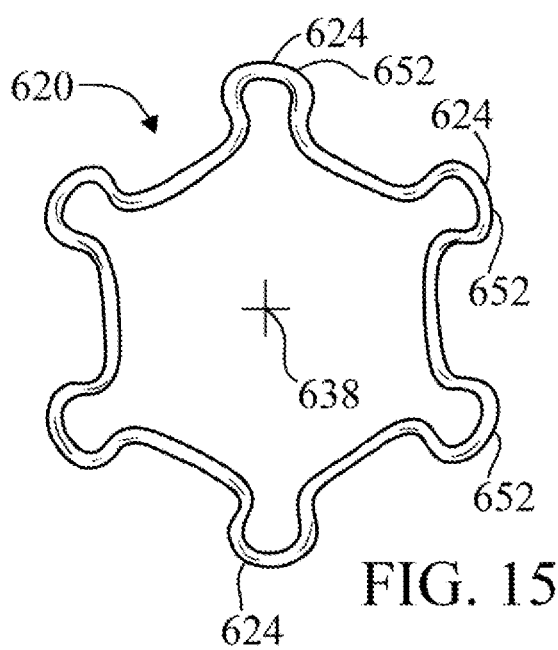
FIG. 15 is another plan view of the multi-lobed tensioning device of FIG. 14, taken with the tensioning device in a stretched state.

FIGS. 14 and 15 show an exemplary multi-lobed dynamic tensioning device 620, taken with the tensioning device in a resting state (FIG. 14) and a stretched state (FIG. 15). Tensioning device has a structural member 644 that extends completely around a central axis 638 to form a closed loop 634 circumferentially bounding a central opening 636. Structural member 644 follows an undulating path to form a plurality of lobes 652 (also called radial protrusions) each providing a suture-coupling site 624. The stretched state is produced by radial expansion of one or more lobes 652 of closed loop 634 away from central axis 638.

Figure 16:
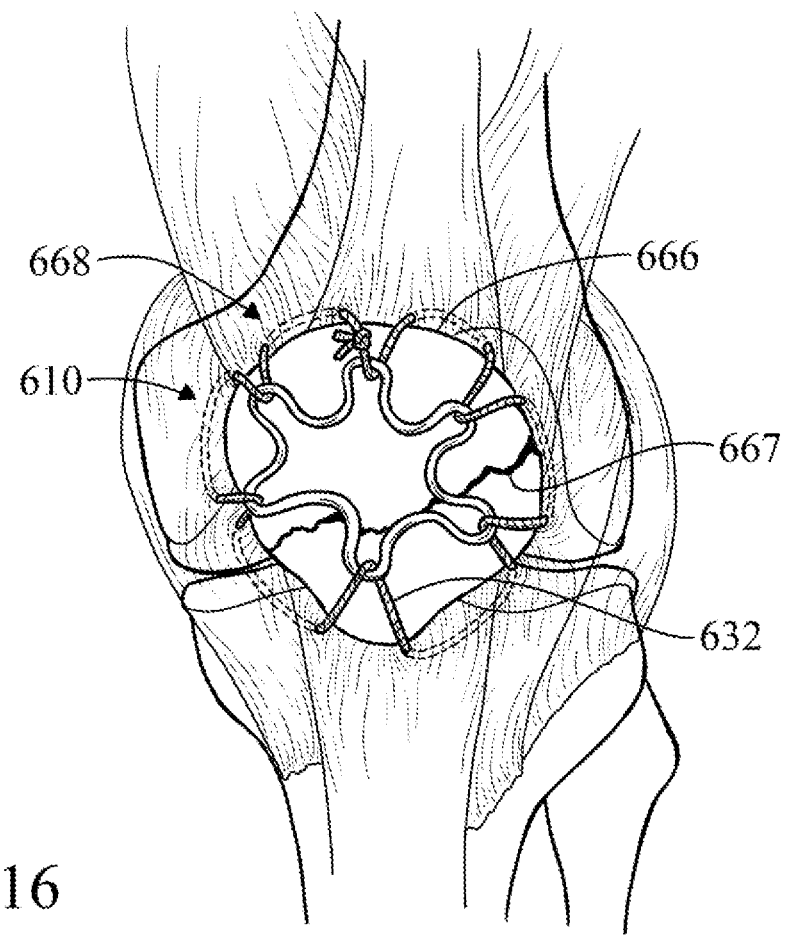
FIG. 16 is an environmental view of an exemplary compression construct fixing a fractured patella and including the multi-lobed tensioning device of FIGS. 14 and 15 connected to soft tissue around the fractured patella using a suture.

FIG. 16 shows an exemplary compression construct 610 fixing a patella 666 having a fracture 667. Compression construct 610 includes tensioning device 620 connected to soft tissue 668 around patella 666 using a suture 632. Tensioning device 620 is retracted radially inward toward central axis 638 to a less-stretched state, intermediate the resting state of FIG. 14 and the stretched state of FIG. 15. This radial retraction applies tension to suture 632, resulting in application of compression on fractured patella 666. Tensioning device 620 may be stretched before placement onto patella 666, and held in the stretched state of FIG. 15 using a retainer while the tensioning device is connected to soft tissue 668 using suture 632, and then the retainer may be removed (also see FIGS. 9 and 10 of Subsection A). Alternatively, or in addition, tensioning device 620 may be stretched in situ on patella 666, such by tightening suture 632, pulling individual lobes 652 or sets of lobes 652 of tensioning device 620 radially outward using a tool (such as a pair of pliers), manually while grasped by the surgeon's hand(s), or a combination thereof, among others. For simplification, only a single suture 632 is depicted in FIG. 16 extending through each of lobes 652. In other examples, more than one suture may be used to connect tensioning device 620 to soft tissue 668, such as a separate suture for each lobe 652, each pair of lobes 652, or the like. In other examples, at least one of the sutures may extend through a tunnel formed in bone and/or may be anchored to bone using a suture anchor (e.g., see below).

Figures 17, 18:
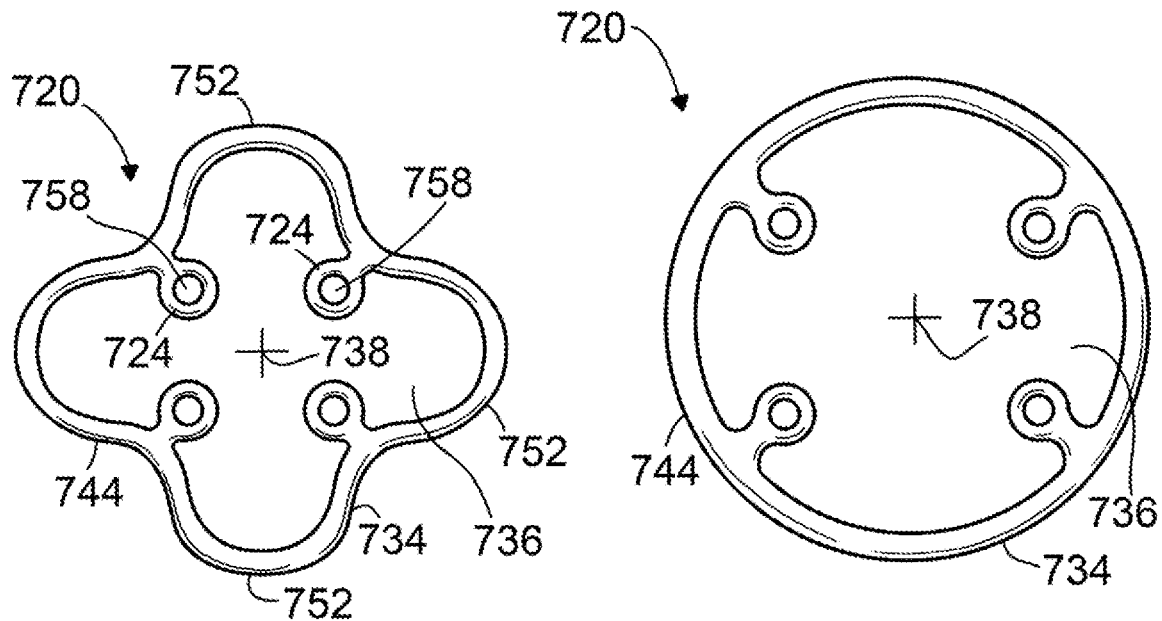
FIG. 17 is a plan view of another exemplary multi-lobed tensioning device taken with the tensioning device in a resting state.
FIG. 18 is another plan view of the multi-lobed tensioning device of FIG. 17, taken with the tensioning device in a stretched state.

FIGS. 17 and 18 show another exemplary multi-lobed tensioning device 720 taken with the tensioning device in a resting state (FIG. 17) and a stretched state (FIG. 18). Tensioning device 720 has a structural member 744 that extends completely around a central axis 738 to form a closed loop 734 circumferentially bounding a central opening 736. Structural member 744 follows an undulating path to form a plurality of lobes 752. Apertures 758 are defined by widened regions of structural member 744 between adjacent pairs of lobes 752, to form suture-coupling sites 724 at the apertures. The stretched state of FIG. 18 is produced by radial expansion of closed loop 734 away from central axis 738, by moving each aperture 758 away from central axis 738.

Figure 19:
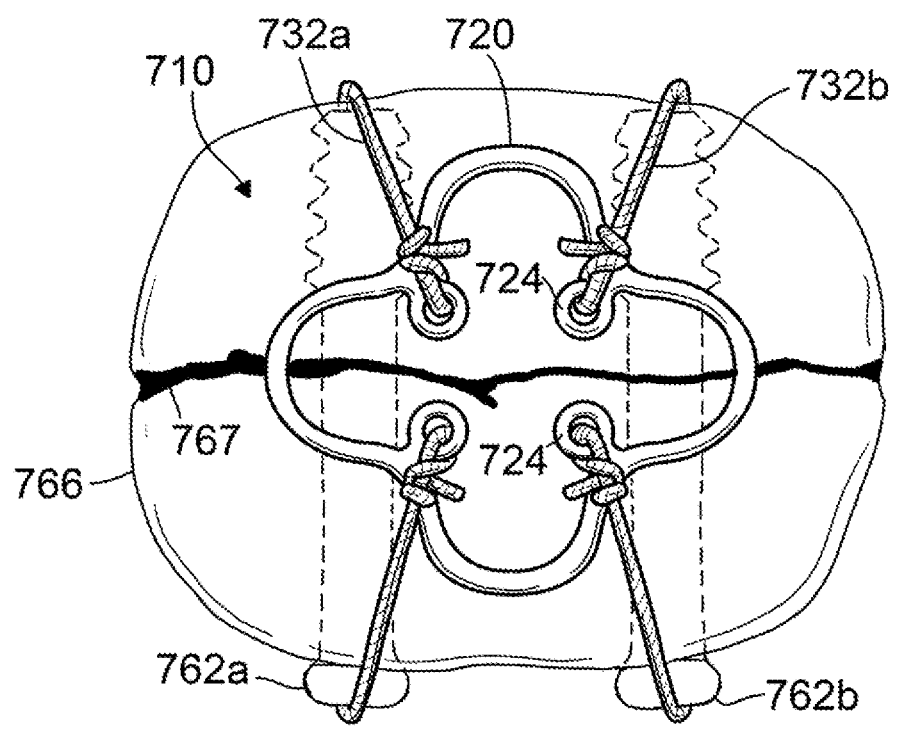
FIG. 19 is an environmental view of an exemplary compression construct fixing a fractured patella and including the multi-lobed tensioning device of FIGS. 17 and 18, suture, and a pair of suture anchors.

FIG. 19 shows an exemplary compression construct 710 fixing a patella 766 having a fracture 767. Compression construct 710 includes tensioning device 720 connected to patella 766 using sutures 732a, 732b and a pair of cannulated fasteners 762a, 762b. Each suture extends through a pair of suture-coupling sites 724 and through one of cannulated fasteners 762a or 762b. Tensioning device 720 is disposed in an intermediate state that is less stretched than the stretched state of FIG. 18 and more stretched than the resting state of FIG. 17. Tensioning device 720 is applying tension to each suture 732a, 732b, resulting in application of compression on fractured patella 766.

C. Dynamic Tensioning Devices Defining a Pair of Apertures

This subsection describes illustrative dynamic tensioning devices each defining a pair of apertures at opposite ends of the device; see FIGS. 20-23.

Figure 20:
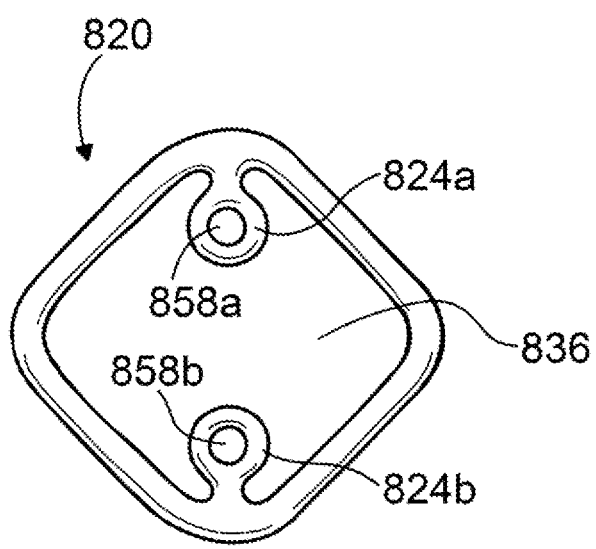
FIGS. 20-23 are plan views of other exemplary dynamic tensioning devices each defining a pair of apertures at opposite ends of the device.

FIG. 20 shows a tensioning device 820 forming a closed loop shaped as a quadrilateral. A pair of apertures 858a, 858b providing suture-coupling sites 824a, 824b (or an anchoring site and a suture-coupling site) are defined at opposite corners of the quadrilateral. In other examples, apertures 858a, 858b may be eliminated, and sutures may extend through a central opening 836 at opposite corners thereof (or any combination of the corners).

Figure 21:
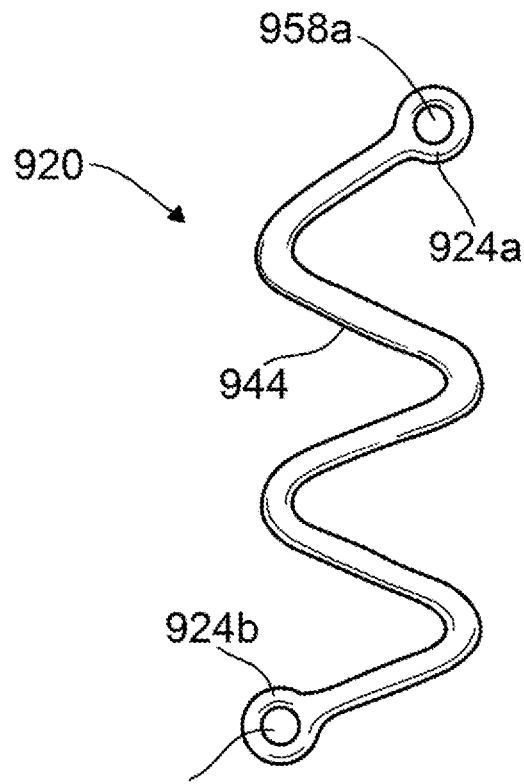

FIG. 21 shows a tensioning device 920 including a structural member 944 extending along a zig-zag, non-looped path between opposite ends of the device. A pair of apertures 958a, 958b providing suture-coupling sites 924a, 924b (or an anchoring site and a suture-coupling site, or a pair of anchoring sites) are defined at opposite ends of structural member 944. Tensioning device 920 is shown in a resting state. When stretched, the distance between apertures 958a, 958b is increased and the size of the angles between linear sections of structural member 944 also increase. In other examples, structural member 944 may follow a wavy, non-looped path between opposite ends of the device.

Figure 22:
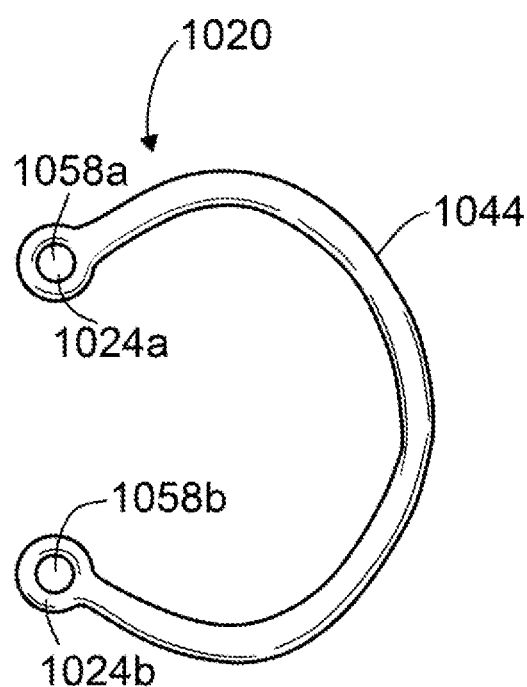

FIG. 22 shows a tensioning device 1020 including a structural member 1044 extending along a C-shaped path between opposite ends of the device. A pair of apertures 1058a, 1058b providing suture-coupling sites 1024a, 1024b (or an anchoring site and a suture-coupling site, or a pair of anchoring sites) are defined at opposite ends of structural member 1044. Tensioning device 1020 is shown in a resting state. When stretched, the distance between apertures 1058a, 1058b is increased and the radius of curvature of structural member 1044 is also increased.

Figure 23:
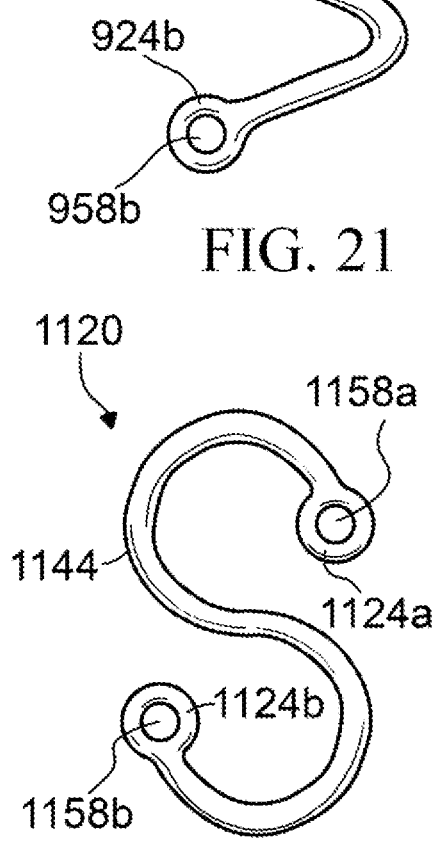

FIG. 23 shows a tensioning device 1120 including a structural member 1144 extending along an S-shaped path between opposite ends of the device. A pair of apertures 1158a, 1158b providing suture-coupling sites 1124a, 1124b (or an anchoring site and a suture-coupling site, or a pair of anchoring sites) are defined at opposite ends of structural member 1144. Tensioning device 1120 is shown in a resting state. When stretched, the distance between apertures 1158a, 1158b is increased and the radius of curvature of structural member 1144 is also increased.

D. Tension Band Fixation

This subsection describes illustrative configurations for tension band fixation of a fractured olecranon using a dynamic compression construct; see FIGS. 24 and 25.

FIG. 24 shows an exemplary compression construct 1210 to fix an olecranon 1269 having a fracture 1270. Compression construct 1210 includes a dynamic tensioning device 1220, a device anchor 1228 (a threaded fastener), a suture 1232 forming a closed loop, and a pair of pins 1271. Pins 1271 are driven into a proximal end of olecranon 1269 and across fracture 1270, along a longitudinal axis of an ulna 1272. Suture 1232 extends around/through hooked ends 1271a of pins 1271 and through a suture-coupling site 1224 defined by a second (proximal) end of tensioning device 1220. A first (distal) end of tensioning device 1220 defines an anchoring site 1222 through which device anchor 1228 is driven into ulna 1272, to fix the translational position of the first end of the tensioning device with respect to the shaft of the ulna. When fully installed, compression construct 1210 is under tension and tensioning device 1220 is in a stretched state. Suture 1232 is dynamically tensioned by tensioning device 1220, because only the first end, and not the second end, of tensioning device 1220 is anchored to the shaft of ulna 1272. As a result, the distance between anchoring site 1222 and suture-coupling site 1224 can vary by deformation of tensioning device 1220 in response to changes in the tension on compression construct 1210, which allows a proximal region of ulna 1272 that spans fracture 1270 to be compressed dynamically by the compression construct.

FIG. 25 shows another exemplary compression construct 1210' being installed to fix fractured olecranon 1269. Compression construct 1210' is identical to compression construct 1210 of FIG. 24, except that tensioning device 1220 has been replaced with tensioning device 1220'. The first end of tensioning device 1220' defines a tool-engagement aperture 1273 adjacent anchoring site 1222. A tool, such as a hinged stretching tool 1274, may be used to stretch tensioning device 1220' in situ on ulna 1272. Jaws 1275a, 1275b of stretching tool 1274 are engaged respectively with tool-engagement aperture 1273 and a bore 1276 formed in ulna. In this configuration, squeezing the handles of stretching tool 1274 applies tension on compression construct 1210', which stretches tensioning device 1220'. While held in this stretched state, device anchor 1228 is installed and then stretching tool 1274 is removed.

E. Multi-Armed Dynamic Tensioning Device

Figure 26:
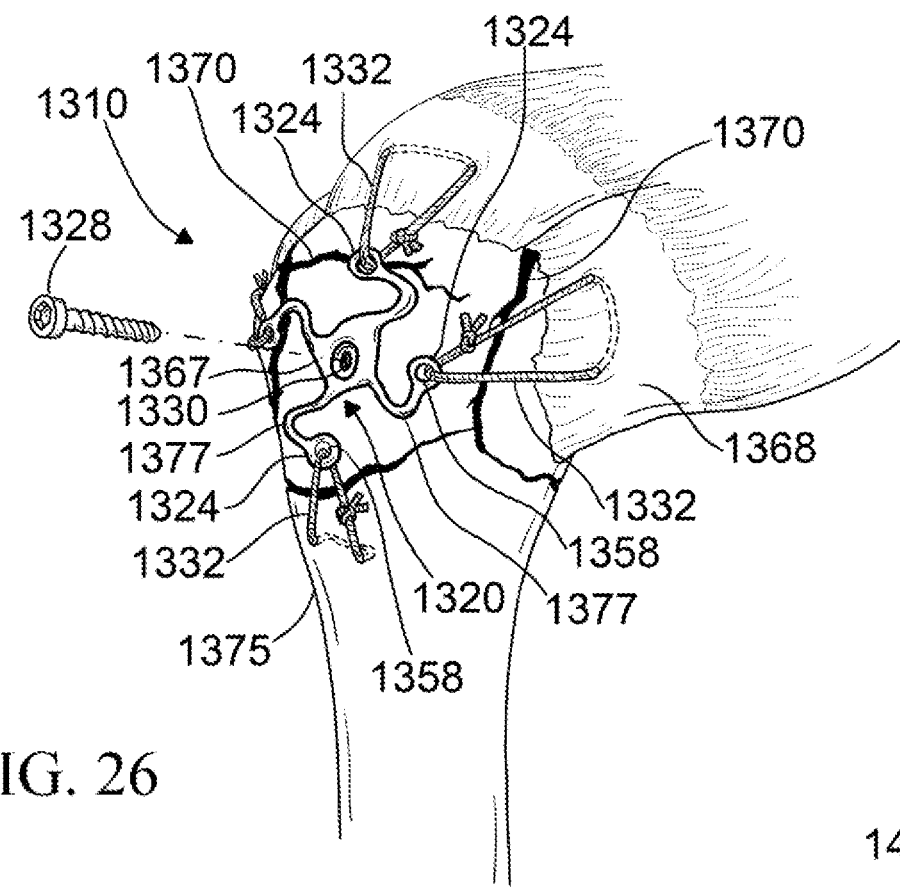
FIG. 26 is a view of an exemplary compression construct fixing a fractured proximal humerus and including a dynamic tensioning device having superelastic arms formed integrally with one another.

This subsection describes an illustrative compression construct 1310 for fixation of a proximal humerus 1375 having multiple fractures 1370; see FIG. 26.

Compression construct 1310 includes a dynamic tensioning device 1320 that is mountable on proximal humerus 1375. Tensioning device 1320 has a body in the form of a central mounting region 1367 defining an aperture 1330 that forms an anchoring site 1322 to receive a device anchor 1328. The device anchor is an externally-threaded fastener in this example. Multiple superelastic arms 1377 project from mounting region 1367 to respective distal ends defining apertures 1358, which provide suture-coupling sites 1324. The superelastic arms are formed integrally with mounting region 1367 in this example, or may be formed as separate pieces that are fastened to a separate mounting piece.

Compression construct 1310 also includes sutures 1332, which are coupled to suture-coupling sites 1324 by extending through apertures 1358. Each suture 1332 is connected to soft tissue 1368 or proximal humerus 1375. The suture may extend through the soft tissue or bone, as shown, or may be attached to the soft tissue or bone using a separate fastener.

F. Compression Construct with Bone Plate and Removable Superelastic Arms

Figure 27:
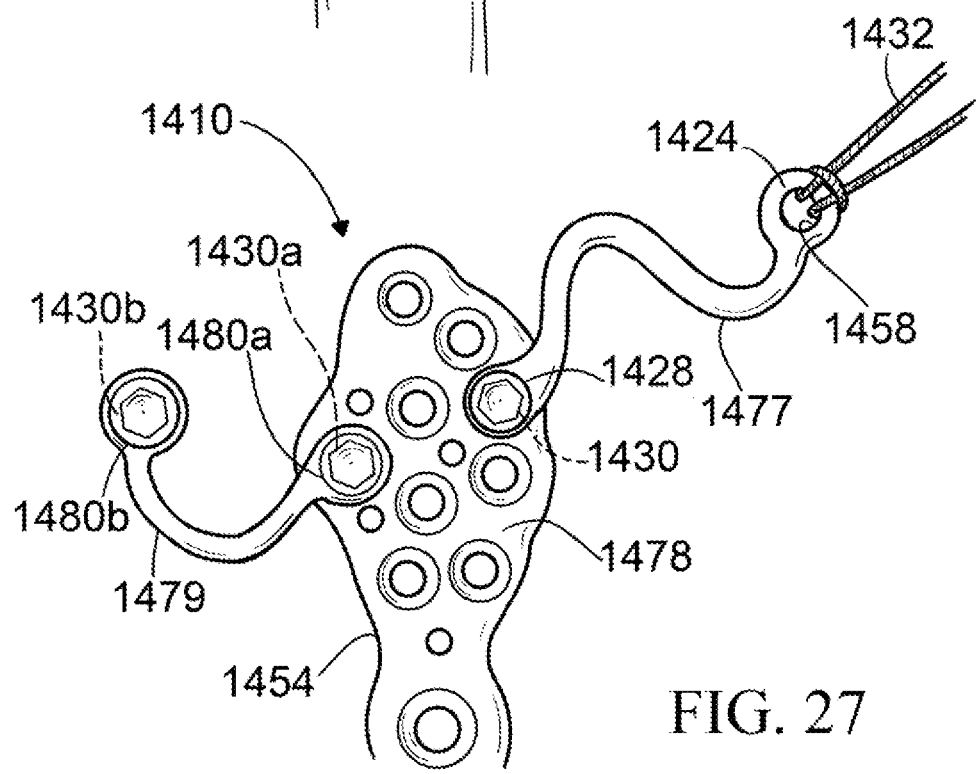
FIG. 27 is a plan view of an exemplary compression construct including a bone plate and a pair of superelastic arms that mount on the bone plate.

This subsection describes an illustrative compression construct 1410 including a bone plate 1454 and a tensioning device 1420 that mounts on an outer surface 1478 of the bone plate; see FIG. 27.

Tensioning device 1420 defines a pair of apertures 1430, 1458 at opposite ends thereof. A device anchor 1428 attaches a first end of the tensioning device to bone plate 1454, where the first end overlaps outer surface 1478. The rest of tensioning device 1420 projects past the lateral periphery of bone plate 1454 (i.e., outside the two-dimensional footprint of the bone plate), to form a superelastic arm 1477. A suture 1432 is connected to a second end of tensioning device 1420 at aperture 1458, which provides a suture-coupling site 1424.

A superelastic outrigger 1479 also may be incorporated into compression construct 1410 and is anchored to bone at both ends. The outrigger defines a pair of apertures 1430a, 1430b at opposite ends thereof. The outrigger is anchored to bone plate 1454 at a first end using a first fastener 1480a in first aperture 1430a, and anchored to underlying bone at a second end using a second fastener 1480b extending into bone from second aperture 1430b.

G. Dynamic Tensioning Devices Having Multiple Closed Loops

Figure 28:
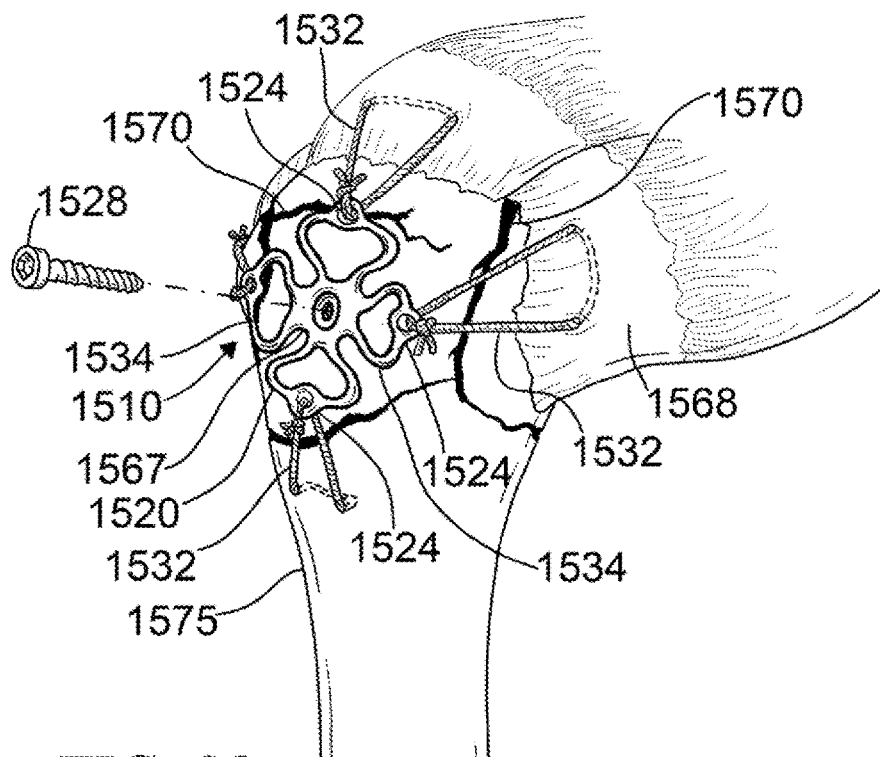
FIG. 28 is a view of an exemplary compression construct fixing a fractured proximal humerus and including a dynamic tensioning device having a plurality of superelastic loops arranged around a central body or mounting region.
Figure 29:
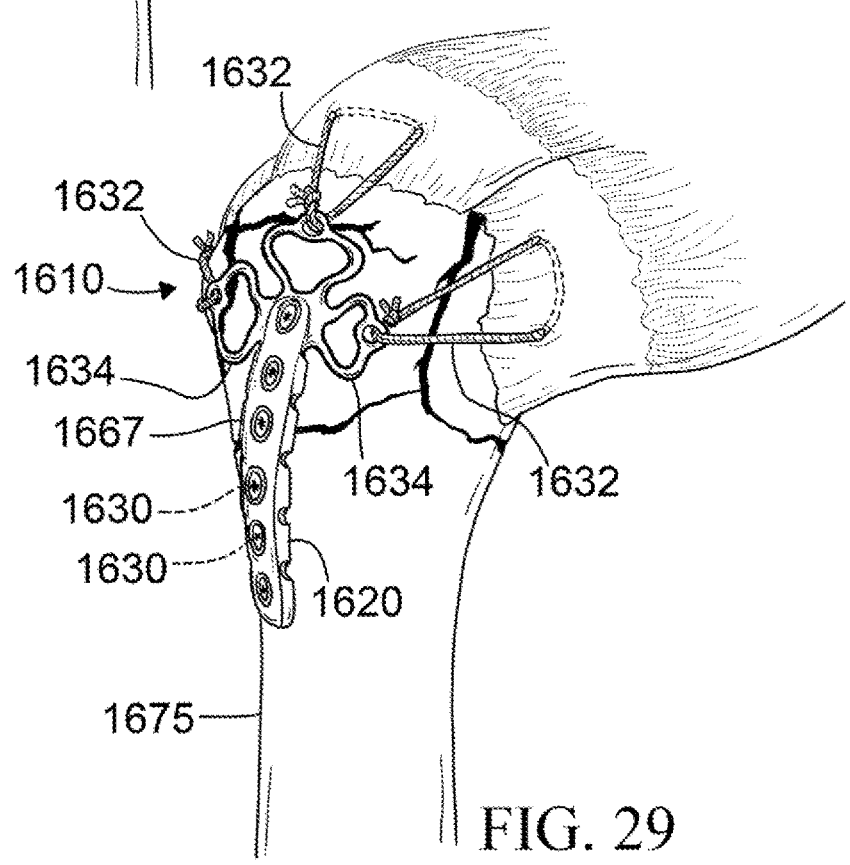
FIG. 29 is a view of another exemplary compression construct fixing a fractured proximal humerus and including a dynamic tensioning device structured as a bone plate including a plurality of superelastic loops projecting from an end of a body of the bone plate.

This subsection describes illustrative dynamic tensioning devices having multiple closed, superelastic loops each formed integrally with the same mounting region and being used in a compression construct to fix a fractured proximal humerus; see FIGS. 28 and 29.

FIG. 28 shows an exemplary compression construct 1510 fixing a fractured proximal humerus 1575. The compression construct includes a dynamic tensioning device having a plurality of superelastic loops 1534 arranged around a central mounting region 1567. (Four superelastic loops 1534 are present in the depicted example.) The superelastic loops and the central mounting region are formed integrally with one another as part of the same plate. Central mounting region 1567 is mounted on proximal humerus 1575 using a device anchor 1528.

Superelastic loops 1534 define respective suture-coupling sites 1524. Sutures 1532 connect the superelastic loops to bone and/or soft tissue, generally as described above for tensioning device 1320 in Subsection E (e.g., see FIG. 26), but with superelastic arms replaced by superelastic loops 1534.

FIG. 29 shows another exemplary compression construct 1610 fixing a fractured proximal humerus 1675. The compression construct includes a tensioning device 1620 structured as a bone plate providing a body 1667 (also called a mounting region) defining a plurality of apertures 1630 for receiving fasteners that mount the body of the bone plate to underlying bone.

Tensioning device 1620 includes a plurality of superelastic loops 1634 projecting from an end of body 1667. (Three superelastic loops 1634 are present in the depicted example.) The superelastic loops are significantly more flexible than body 1667. Superelastic loops 1634 define suture-coupling sites 1624. Sutures 1632 connect the superelastic loops to bone and/or soft tissue, generally as described above for tensioning device 1320 in Subsection E (e.g., see FIG. 26), but with superelastic arms replaced by superelastic loops 1634.

H. Prosthesis-Mountable Dynamic Tensioning Device

Figure 30:
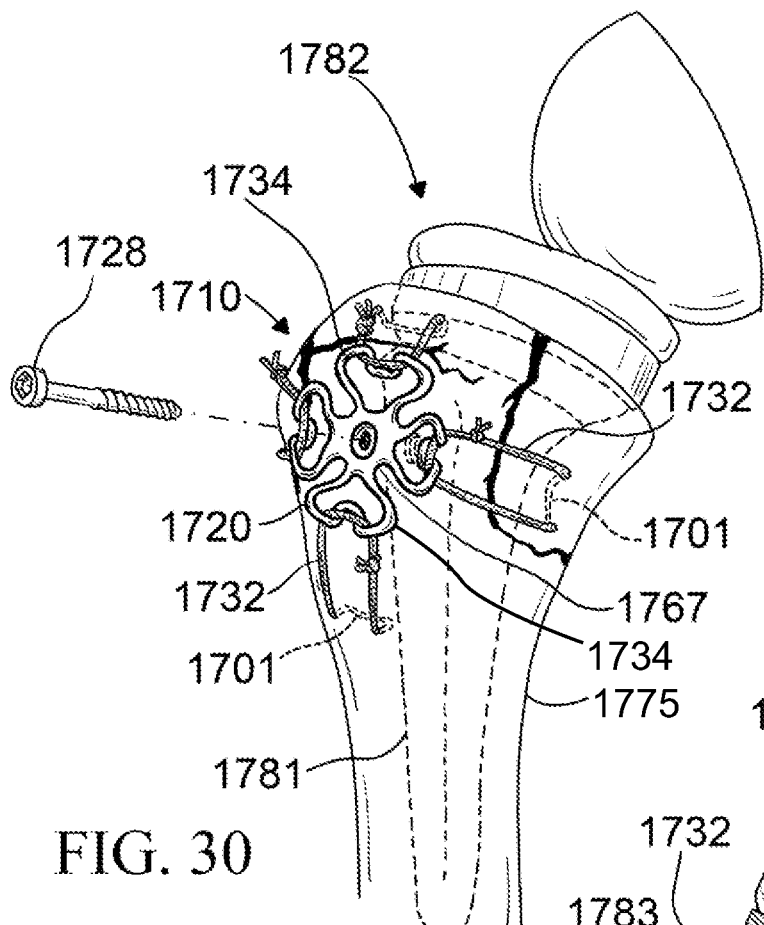
FIG. 30 is view of an exemplary compression construct including a dynamic tensioning device that mounts to a prosthesis installed in a fractured proximal humerus.
Figure 31:
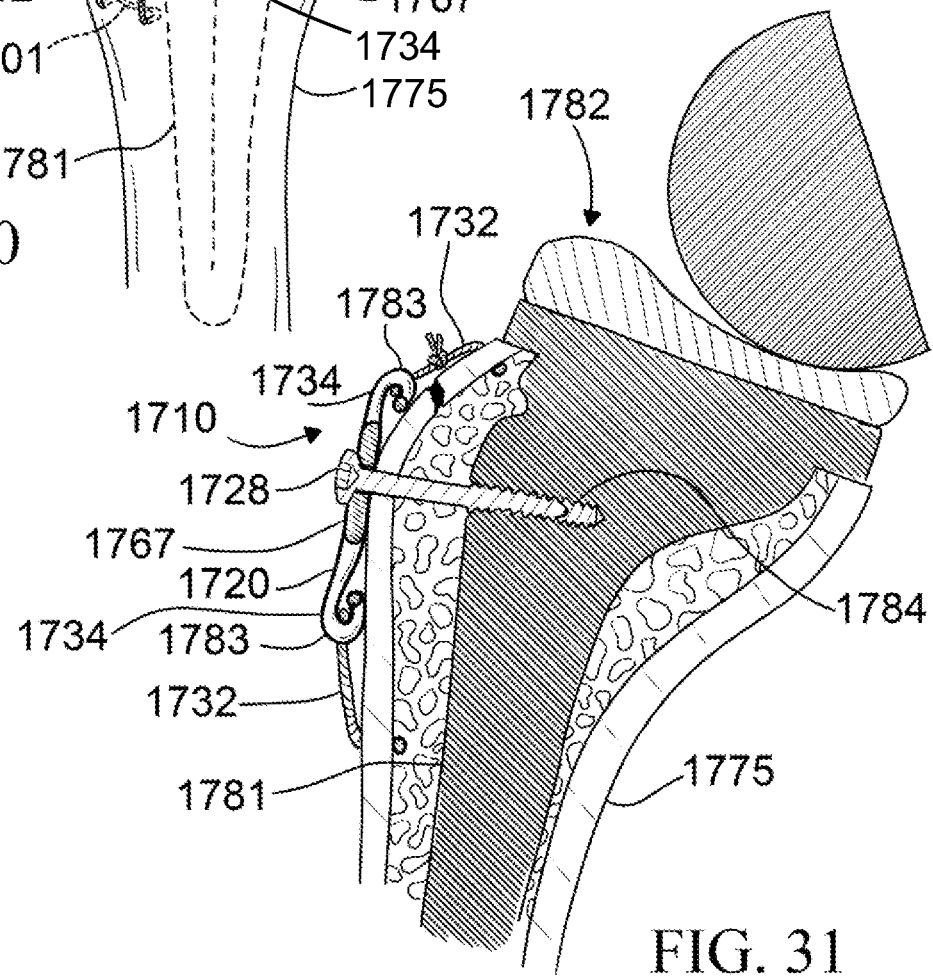
FIG. 31 is a sectional view of the prosthesis, dynamic tensioning device, and fractured proximal humerus of FIG. 30, taken with the dynamic tensioning device mounted to a stem of the prosthesis.

This subsection describes an illustrative dynamic tensioning device 1720 being used in conjunction with a stem 1781 of a reverse prosthesis 1782 in a compression construct 1710 to fix a fractured proximal humerus 1775; see FIGS. 30 and 31.

Tensioning device 1720 is generally similar to tensioning device 1520 described above in Subsection G (also see FIG. 28). For example, tensioning device 1720 has a plurality of superelastic loops 1734 each formed integrally with a central mounting region 1767. However, each superelastic loop 1734 has a hook structure 1783, instead of an aperture, for coupling a suture 1732 to the superelastic loop. The hook structure allows tensioning device 1720 to be hooked radially onto a suture, without receiving a free end, if any, of the suture. A tensioning device utilizing hook structures is described below in more detail in Subsection J.

Mounting region 1767 is mountable to stem 1781 of reverse prosthesis 1782 using a device anchor 1728. Stem 1781 defines an internally threaded bore 1784 that is engaged with a complementary external thread of device anchor 1728 (see FIG. 31).

Each suture 1732 may be connected to proximal humerus 1775 at a position spaced from its corresponding superelastic loop 1734 by extending through a tunnel 1701 formed in proximal humerus 1775, as shown, or by using a separate a suture anchor (e.g., a threaded suture fastener) that extends into the proximal humerus, among others.

I. Bone Plate and Overlying Tensioning Device

This subsection describes illustrative compression constructs including a bone plate coupled to an overlying dynamic tensioning device; see FIGS. 32, 32A, 33, and 33A.

FIG. 32 shows a compression construct 1810 including a bone plate 1854, a dynamic tensioning device 1820, and sutures 1832. Dynamic tensioning device 1820 is mounted on an outer surface 1878 of the bone plate using a device anchor 1828 extending through an aperture of the tensioning device and into an aperture of the bone plate.

Tensioning device 1820 forms a plurality of superelastic loops 1834 projecting radially from a central mounting region 1867 of the tensioning device (see FIGS. 32 and 32A). Each superelastic loop 1834 may be sized such that the loop in a stretched state does not project past the edge of bone plate 1854. Accordingly, tensioning device 1820 may be located at least predominantly or completely within the two-dimensional footprint of bone plate 1854.

Each suture 1832 is coupled to one of superelastic loops 1834. The suture 1832 extends through a pair of holes 1884 defined by bone plate 1854 (see FIG. 32). More specifically, the suture extends through one of the holes, into and/or through one of superelastic loops 1834, and through the other of the holes (see FIGS. 32 and 32A). Depressions 1885 formed in an inner surface 1886 of bone plate 1854 under holes 1884 allow the suture to slide through the holes after bone plate 1854 has been mounted on bone.

FIG. 32A shows tensioning device 1820 taken in isolation. A stretched state of the tensioning device is depicted in solid lines and a resting state in broken lines.

FIG. 33 shows another compression construct 1910 including a bone plate 1954, a dynamic tensioning device 1920, and sutures 1932. Dynamic tensioning device 1920 is formed as a closed loop that fits around bone plate 1954 (see FIGS. 33 and 33A). A base portion 1987 of tensioning device 1920 is located in a groove 1988 formed in an inner surface 1986 of bone plate 1954. A suture-coupling portion 1989 is located on an outer surface 1978 of bone plate 1954. Suture-coupling portion 1989 forms lobes 1952 defining suture-coupling sites 1924.

FIG. 33A shows tensioning device 1920 taken in isolation. A stretched state of the tensioning device is depicted in solid lines and a resting state in broken lines.

J. Clip-On Dynamic Tensioning Device

This subsection describes an illustrative dynamic tensioning device 2020 that clips onto a pair of suture regions 2090a, 2090b of a compression construct 2010; see FIGS. 34-37.

Figure 34:
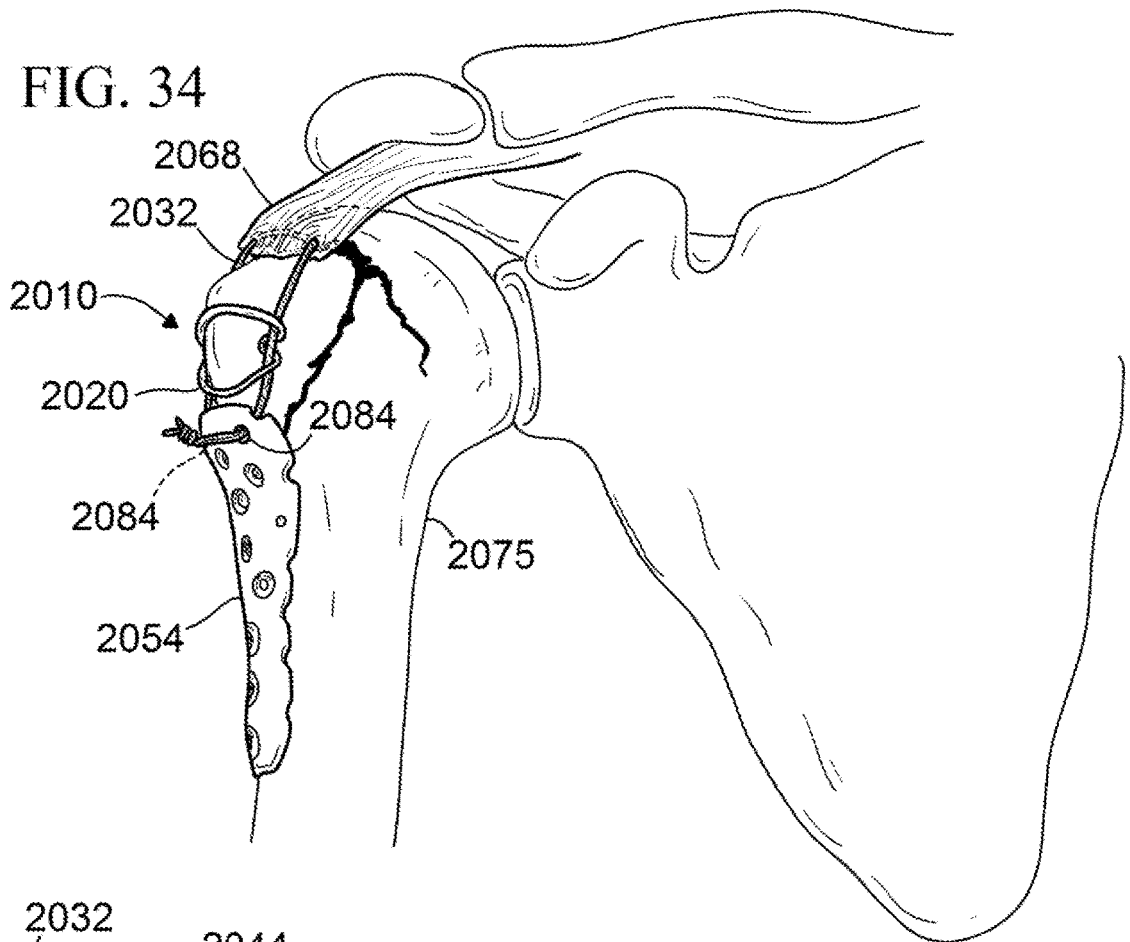
FIG. 34 is a view of a fractured proximal humerus being fixed with a compression construct including a suture tensioned using a clip-on dynamic tensioning device hooked radially onto a pair of regions of the suture.

FIG. 34 shows a fractured proximal humerus 2075 being fixed with compression construct 2010. The compression construct includes a bone plate 2054 mounted to proximal humerus 2075 using fasteners, and a suture 2032 extending through holes 2084 defined by bone plate 2054. The suture 2032 extends through soft tissue 2068 (a supraspinatus tendon) and forms a closed loop. The suture defines a longitudinal axis along which the suture is elongated. The term "radial" with respect to a region along a suture means orthogonal to the longitudinal axis defined by the suture at the region.

Figures 35, 36, 37:
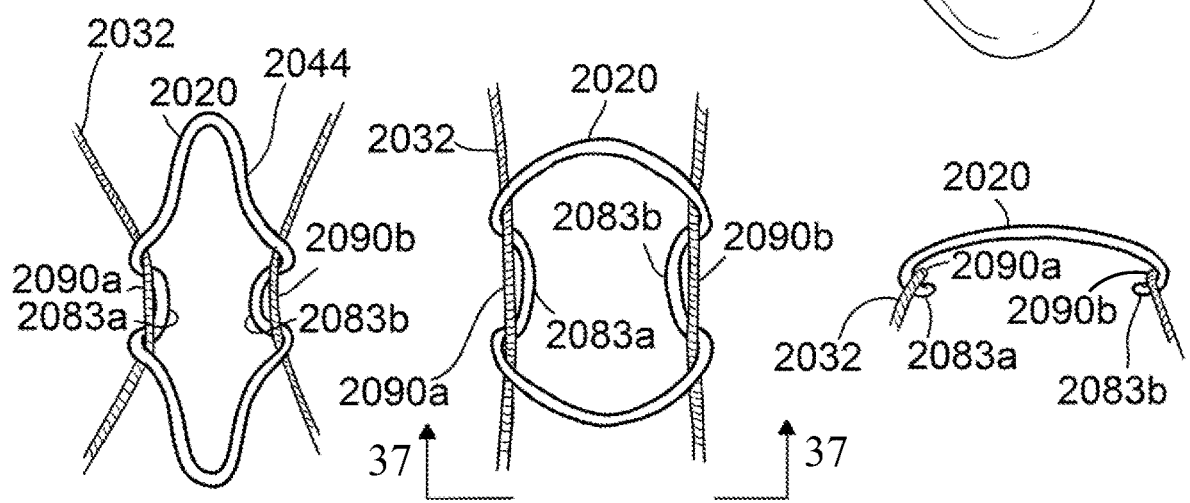
FIG. 35 is a fragmentary plan view of the compression construct of FIG. 34 taken in isolation with the dynamic tensioning device applying tension to the suture.
FIG. 36 is another fragmentary plan view of the compression construct of FIG. 34 taken with the tensioning device held in a stretched state.
FIG. 37 is an edge view of the clip-on dynamic tensioning device of FIG. 36 in the stretched state, taken generally along line 37-37 of FIG. 36.

Tensioning device 2020 has a pair of hook structures 2083a, 2083b formed opposite one another (see FIGS. 35-37). In the example depicted, tensioning device 2020 is formed as a closed loop by a structural member 2044. Each hook structure 2083a, 2083b is configured to receive a suture region 2090a or 2090b by radial motion of the suture region into the hook structure (and/or radial motion of the hook structure onto the suture region). Accordingly, hook structures 2083a, 2083b allow a suture to be coupled to tensioning device 2020 after the suture has been installed and initially tensioned.

FIG. 35 shows tensioning device 2020 hooked into suture regions 2090a, 2090b and applying tension to suture 2032 by urging suture regions 2090a, 2090b toward one another radially. Suture regions 2090a, 2090b may be provided by the same suture or different sutures.

FIGS. 36 and 37 shows tensioning device 2020 in a stretched state, with both suture regions 2090a, 2090b located in hook structures 2083a, 2083b. Tensioning device 2020 is being held in the stretched state and thus is not yet applying tension to suture regions 2090*a*, 2090*b*.

K. In-Bone Dynamic Tensioning Devices

This subsection describes illustrative dynamic tensioning devices that extend into a tunnel formed in bone; see FIGS. 38-41.

Figure 38:
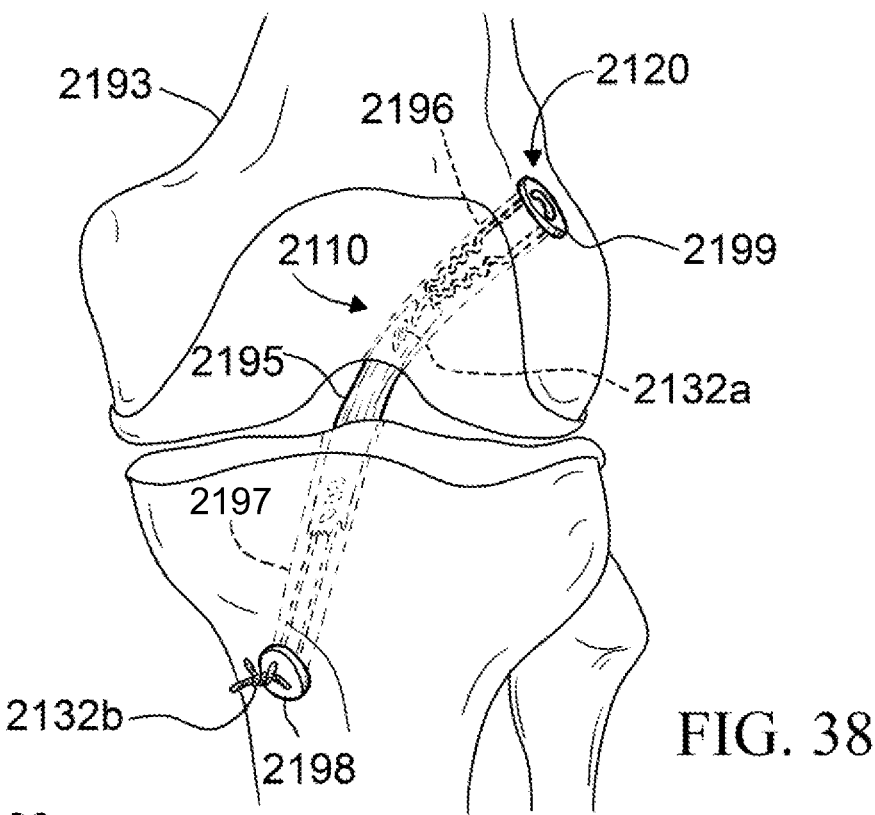
FIG. 38 is a view of a knee joint and a compression construct extending through the knee joint and including a ligament graft connected at one end, via a suture, to a dynamic tensioning device disposed at least partially in a bone tunnel.

FIG. 38 shows a knee joint 2192 formed between a femur 2193 and a tibia 2194. A compression construct 2110 is connected to the knee joint and includes a ligament graft 2195. The compression construct extends through a femoral tunnel 2196, across knee joint 2192, and through a tibial tunnel 2197. An upper end of ligament graft 2195 is connected to a first suture 2132*a*, and a lower end of the ligament graft is connected to a second suture 2132*b*. First suture 2132*a* connects ligament graft 2195 to a tensioning device 2120 engaged with a surface of femur 2193. Second suture 2132*b* connects ligament graft 2195 to a button 2198 engaged with a surface of tibia 2194.

Figures 39, 40, 41:
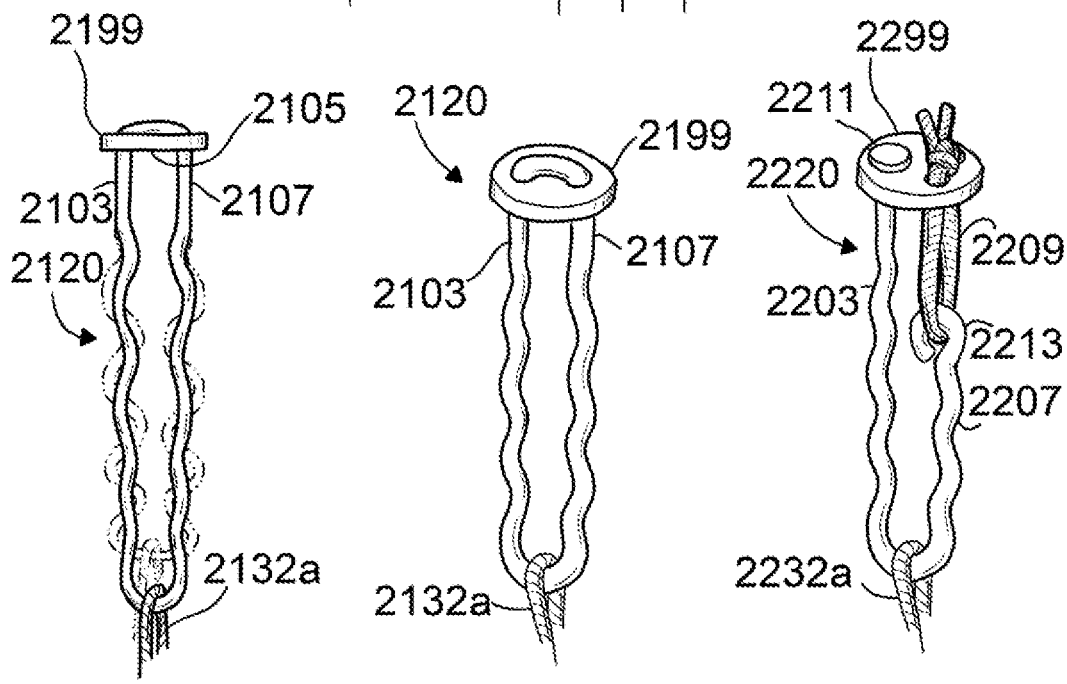
FIG. 39 is a fragmentary side view of the compression construct of FIG. 38, taken around the dynamic tensioning device with the tensioning device shown in a stretched state (solid lines) and a resting state (broken lines).
FIG. 40 is another fragmentary view of the compression construct of FIG. 38, taken around the dynamic tensioning device in a stretched state.
FIG. 41 is a side view of another exemplary dynamic tensioning device for the compression construct of FIG. 38, where the tensioning device has a superelastic loop of adjustable length.

Tensioning device 2120 includes a button 2199 connected to a superelastic loop 2103 (see FIGS. 38-40). Button 2199 has an inner surface 2105 that engages a surface of femur 2193. Superelastic loop 2103 projects transversely from inner surface 2105 into femoral tunnel 2196 and forms a suture-coupling site 2124 at an end of loop 2103. First suture 2132*a* extends through loop 2103. Button 2199 is sized such that the button cannot enter femoral tunnel 2196 when inner surface 2105 is facing an inlet of femoral tunnel 2196. In some examples, button 2199 may be shaped such that the button can pass through the femoral tunnel when properly oriented. In some examples, button 2199 and superelastic loop 2103 may be formed integrally with one another. In some examples, button 2199 may be formed separately from superelastic loop, and may be composed of a material that is not superelastic.

Superelastic loop 2103 may be changed from a resting state to a stretched state by applying tension to superelastic loop 2103 while it is located in femoral tunnel 2196. For example, second suture 2132*b* may be tensioned from outside a lower end of tibial tunnel 2197, which results in force transmission to superelastic loop 2103.

FIG. 39 shows tensioning device 2120 connected to first suture 2132*a*. Tensioning device 2120 is depicted in a stretched state (solid lines) and a resting state (broken lines). A superelastic member 2107 forms loop 2103 and extends along a wavy path (also see FIG. 40).

FIG. 41 shows another exemplary tensioning device 2220 for use in compression construct 2110 (also see FIG. 38). Tensioning device 2220 has a superelastic loop 2203 connected to a suture 2232*a*. Superelastic loop 2203 includes a superelastic member 2207 and a securing member 2209. Superelastic member 2207 extends along a path between a fixed end 2211 and a free end 2213. Fixed end 2211 is attached to button 2299. Free end 2213 is connected to button 2299 using securing member 2209. In the example depicted, securing member 2209 is a suture. The length of securing member 2209, measured between button 2299 and free end 2213 of superelastic member 2207, is determined when the securing member is tied off. Accordingly, securing member 2209 can be used to apply and adjust the tension on compression construct 2210, by adjusting the length of superelastic loop 2203 formed collectively by superelastic member 2207 and securing member 2209.

IV. Illustrative Combinations and Additional Examples

This section describes additional aspects and features of the compression constructs, dynamic tensioning devices, and associated methods, presented without limitation as a series of paragraphs, some or all of which may be alphanumerically indexed for clarity and efficiency. Each of these paragraphs can be combined with one or more other paragraphs, and/or with disclosure from elsewhere in this application, in any suitable manner. Some of the paragraphs below expressly refer to and further limit other paragraphs, providing without limitation examples of some of the suitable combinations.

A1. A construct to compress tissue, comprising: a dynamic tensioning device configured to be implanted in a subject and defining a suture-coupling site, the dynamic tensioning device being deformable superelastically from a resting state to a stretched state; and a suture connected to the dynamic tensioning device at the suture-coupling site.

A2. The construct of paragraph A1, wherein the suture-coupling site is a first suture-coupling site, wherein the dynamic tensioning device defines a second suture-coupling site and/or an aperture, and wherein a distance between the first suture-coupling site and the second suture-coupling site and/or the aperture is increased in the stretched state relative to the resting state.

A3. The construct of paragraph A1 or A2, further comprising a retainer coupled or configured to be coupled to the dynamic tensioning device to hold the dynamic tensioning device in the stretched state until the retainer is removed and/or disabled.

A4. The construct of any of paragraphs A1 to A3, wherein the dynamic tensioning device is composed of an alloy including nickel and titanium.

A5. The construct of any of paragraphs A1 to A4, wherein the suture includes cord, wire, tape, and/or cable, and/or wherein the suture has only a single strand/filament or is composed of two or more strands/filaments, optionally, two or more strands/filaments that are entwined with one another.

A6. The construct of any of paragraphs A1 to A5, further comprising a needle connected to the dynamic tensioning device via the suture.

A7. The construct of any of paragraphs A1 to A6, further comprising a fastener configured to engage bone and connected to the dynamic tensioning device via the suture or another suture.

A8. The construct of any of paragraphs A1 to A7, wherein the suture is a first suture coupled to a first suture-coupling site of the dynamic tensioning device, wherein the dynamic tensioning device defines a second suture-coupling site, and wherein the construct further comprises a second suture connected to the dynamic tensioning device at the second suture-coupling site.

A9. The construct of any of paragraphs A1 to A8, wherein the dynamic tensioning device defines an aperture that is spaced from the suture-coupling site, the construct further comprising a fastener configured to extend through the aperture and into bone, to attach the dynamic tensioning device to the bone.

A10. The construct of any of paragraphs A1 to A9, wherein the dynamic tensioning device has an outer surface opposite an inner surface that is configured to face bone, wherein a central axis extends through the dynamic tensioning device transverse to the outer and inner surfaces, and wherein the dynamic tensioning devices includes a structural member extending completely around the central axis to form a closed loop defining a central opening.

A11. The construct of paragraph A10, wherein a length and/or a width of the central opening is greater than a width of the structural member measured in a plane orthogonal to the central axis.

A12. The construct of paragraph A10 or A11, wherein a distance from the structural member to the central axis varies along the structural member to form a plurality of protrusions each projecting away from the central axis, and wherein each protrusion defines a suture-coupling site.

A13. The construct of any of paragraphs A10 to A12, wherein the dynamic tensioning device defines an aperture separate from the central opening and extending from the outer surface to the inner surface.

A14. The construct of paragraph A13, wherein the dynamic tensioning device defines two or more apertures each extending from the outer surface to the inner surface and spaced from the central opening.

A15. The construct of any of paragraphs A1 to A14, wherein the dynamic tensioning device has a first end opposite a second end, wherein each of the first end and the second end defines an aperture.

A16. The construct of any of paragraphs A1 to A15, further comprising: an orthopedic implant selected from a bone plate, an intramedullary nail, and a prosthesis; and a fastener configured to mount the dynamic tensioning device to the orthopedic implant.

A17. The construct of any of paragraphs A1 to A16, wherein the dynamic tensioning device includes a button having an inner surface configured to be placed on bone over an end of a tunnel formed in the bone, and also includes a superelastic member connected to the button and configured to project into the tunnel from an inner surface of the button and forming the suture-coupling site.

A18. The construct of any of paragraphs A1 to A17, wherein the suture-coupling site includes a hook structure configured to be hooked radially onto a suture.

A19. The construct of paragraph A18, wherein the dynamic tensioning device includes a pair of hook structures configured to be hooked onto a pair of suture sections to urge the pair of suture sections toward one another radially.

A20. The construct of any of paragraphs A1 to A19, wherein the dynamic tensioning device is provided by a plate, wherein the plate includes a mounting region defining one or more apertures to attach the mounting region to bone and also includes two or more superelastic loops or superelastic arms connected to the mounting region and each defining a suture-coupling site.

A21. The construct of paragraph A20, wherein the two or more superelastic loops or superelastic arms and the mounting region are formed collectively as a single piece.

A22. The construct of any of paragraphs A1 to A21, wherein the dynamic tensioning device includes three or more predefined suture-coupling sites.

A23. The construct of any of paragraphs A1 to A22, wherein the superelastic tensioning device is formed as a single piece and configured to be operative without extending into bone.

A24. The construct of any of paragraphs A1 to A23, wherein the superelastic tensioning device has an inner surface to face bone, and wherein the inner surface is free of protrusions for entering the bone.

A25. The construct of any of paragraphs A1 to A24, wherein the suture is composed of metal, synthetic/natural polymer(s), or a combination thereof.

B1. A method of tissue compression, the method comprising: selecting a dynamic tensioning device that is deformable superelastically from a resting state to a stretched state; and connecting a first tissue or tissue portion and a second tissue or tissue portion to one another using the dynamic tensioning device coupled to one or more sutures and disposed in the stretched state.

B2. The method of paragraph B1, wherein the dynamic tensioning device is under tension when connecting is completed.

B3. The method of paragraph B2, wherein the dynamic tensioning device is held in the stretched state by a retainer, further comprising removing or disabling the retainer after connecting.

B4. The method of paragraph B3, wherein removing or disabling the retainer results in tension or increased tension on the one or more sutures.

B5. The method of paragraph B3 or B4, further comprising coupling the retainer to the dynamic tensioning device before connecting.

B6. The method of any of paragraphs B1 to B5, wherein the dynamic tensioning device is placed in the stretched state during a surgical procedure in which the dynamic tensioning device is implanted in a subject.

B7. The method of paragraph B6, wherein the dynamic tensioning device is placed in the stretched state by applying tension to the dynamic tensioning device via at least one of the one or more sutures.

B8. The method of paragraph B6, wherein the dynamic tensioning device is placed in the stretched state by applying tension to the dynamic tensioning device using a tool engaged with the dynamic tensioning device during the surgical procedure.

B9. The method of any of paragraphs B1 to B8, wherein the first tissue or tissue portion includes a bone or bone fragment, and wherein connecting includes securing one of the one or more sutures to the bone or bone fragment.

B10. The method of any of paragraphs B1 to B9, wherein the second tissue or tissue portion is soft tissue.

B11. The method of paragraph B10, wherein the soft tissue includes tendon, ligament, or muscle.

B12. The method of any of paragraphs B1 to B8, B10, and B11, wherein the first tissue or tissue portion includes tendon, ligament, or muscle.

B13. The method of any of paragraphs B1 to B12, wherein connecting includes mounting the dynamic tensioning device to an orthopedic implant selected from a bone plate, an intramedullary nail, and a prosthesis.

B14. The method of paragraph B13, wherein the dynamic tensioning device has a first end and a second end, and wherein connecting includes mounting the first end to the orthopedic implant and connecting the second end to a suture of the one or more sutures.

B15. The method of any of paragraphs B1 to B14, wherein connecting includes securing the dynamic tensioning device to bone using a fastener that extends from an aperture of the dynamic tensioning device and into the bone.

B16. The method of any of paragraphs B1 to B15, wherein each suture independently includes cord, wire, tape, or cable, and/or wherein each suture independently has only a single strand/filament or is composed of two or more strands/filaments.

B17. The method of any of paragraphs B1 to B16, further comprising any limitation or combination of limitations of any of paragraphs A1 to A25.

V. Advantages and Benefits

The different examples of compression constructs, dynamic tensioning devices, and associated methods provide several advantages over known solutions for compressing tissue. For example, illustrative examples described herein dynamically tension a suture(s), to maintain a more constant tension on the suture(s) during healing and normal activity.

Additionally, and among other benefits, illustrative examples described herein provide better surgical outcomes and offer more options for design of compression constructs.

Additionally, and among other benefits, illustrative examples described herein dampen shocks and vibrations to reduce the chance of tissue damage.

Additionally, and among other benefits, illustrative examples described herein enable a more customizable compression of bone.

Additionally, and among other benefits, illustrative examples described herein enable dynamic compression of a soft tissue graft, such as a ligament or tendon graft.

No known constructs, devices, or methods can perform these functions. However, not all examples described herein provide the same advantages or the same degree of advantage.

VI. Conclusion

The disclosure set forth above may encompass multiple distinct examples with independent utility. Although each of these has been disclosed in its preferred form(s), the specific examples thereof as disclosed and illustrated herein are not to be considered in a limiting sense, because numerous variations are possible. To the extent that section headings are used within this disclosure, such headings are for organizational purposes only. The subject matter of the disclosure includes all novel and nonobvious combinations and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

I claim:

1. A construct to compress tissue, comprising:
   a dynamic tensioning device configured to be implanted in a subject and defining a plurality of suture-coupling sites, the dynamic tensioning device being deformable superelastically from a resting state to a stretched state; and
   a plurality of sutures configured to couple to the dynamic tensioning device at each of the plurality of suture-coupling sites,
   wherein:
      the dynamic tensioning device defines a first suture-coupling site and a second suture-coupling site of the plurality of suture-coupling sites with a structural member therebetween;
      the plurality of suture-coupling sites are disposed radially around a centrally located mounting aperture formed by the structural member and configured for anchoring the dynamic tensioning device; and
      a distance between each of the first suture-coupling site and the second suture-coupling site with the mounting aperture is increased in the stretched state relative to the resting state.

2. The construct of claim 1, further comprising a needle connected to the dynamic tensioning device via at least one of the plurality of sutures.

3. The construct of claim 1, further comprising a fastener configured to engage bone and connected to the dynamic tensioning device via at least one of the plurality of sutures.

4. The construct of claim 1, wherein the plurality of sutures comprise a first suture configured to couple to the first suture-coupling site of the dynamic tensioning device, and wherein the plurality of sutures further comprise a second suture configured to couple to the dynamic tensioning device at the second suture-coupling site.

5. The construct of claim 4, wherein the construct comprises a fastener configured to extend through the mounting aperture and into bone, to attach the dynamic tensioning device to the bone.

6. The construct of claim 5, wherein the dynamic tensioning device has an outer surface opposite an inner surface that is configured to face bone, wherein a central axis extends through the dynamic tensioning device transverse to the outer and inner surfaces.

7. The construct of claim 6, wherein a distance from the structural member to the central axis varies along the structural member to form a plurality of protrusions each projecting away from the central axis, and wherein each protrusion defines one of the plurality of suture-coupling sites.

8. The construct of claim 7, wherein the dynamic tensioning device defines two or more apertures each extending from the outer surface to the inner surface and spaced from the mounting aperture.

9. The construct of claim 4, wherein:
   the plurality of suture-coupling sites further comprises a third suture-coupling site and a fourth suture-coupling site;
   a third suture of the plurality of sutures is connected to the third suture-coupling site; and
   a fourth suture of the plurality of sutures connected to the fourth suture-coupling site.

10. The construct of claim 9, further comprising a bone screw for passing through the mounting aperture to anchor the dynamic tension device.

11. The construct of claim 1, further comprising a third suture-coupling site of the plurality of suture-coupling sites.

12. The construct of claim 11, wherein the dynamic tensioning device is formed as a single piece and configured to be operative without extending into bone.

13. The construct of claim 12, wherein the dynamic tensioning device has an inner surface to face bone, and wherein the inner surface is free of protrusions for entering the bone.

* * * * *